United States Patent [19]

Kerr et al.

[11] Patent Number: 5,648,210
[45] Date of Patent: Jul. 15, 1997

[54] NUCLEOTIDE SEQUENCES OF GALACTINOL SYNTHASE FROM ZUCCHINI AND SOYBEAN

[75] Inventors: Phillip S. Kerr; Richard W. Pearlstein, both of Newark; Bruce J. Schweiger, Wilmington, all of Del.; Mary F. Becker-Manley, Beacon, N.Y.; John W. Pierce, Wilmington, Del.

[73] Assignee: E. I. Du Pont de Nemours and Company, Wilmington, Del.

[21] Appl. No.: 182,060
[22] PCT Filed: Jul. 24, 1992
[86] PCT No.: PCT/US92/06057
§ 371 Date: Aug. 23, 1994
§ 102(e) Date: Aug. 23, 1994
[87] PCT Pub. No.: WO93/02196
PCT Pub. Date: Feb. 4, 1993

[51] Int. Cl.$^6$ .......................... C12Q 1/68; C07H 21/02; C07H 21/04; C12P 19/34
[52] U.S. Cl. .................. 435/6; 536/23.1; 536/24.3; 536/23.2; 536/23.6; 435/91.2
[58] Field of Search .................... 435/6, 91.2; 536/23.1, 536/24.3, 23.2, 23.6

[56] References Cited

U.S. PATENT DOCUMENTS

| | | | |
|---|---|---|---|
| 2,881,076 | 4/1959 | Sair | 99/14 |
| 3,142,571 | 7/1964 | McAnelly | 99/14 |
| 4,088,795 | 5/1978 | Goodnight, Jr. et al. | 426/598 |
| 4,420,425 | 12/1983 | Lawhon | 260/123.5 |
| 4,490,406 | 12/1984 | Ferrero et al. | |
| 4,645,677 | 2/1987 | Lawhon et al. | 426/431 |

FOREIGN PATENT DOCUMENTS

| | | | |
|---|---|---|---|
| 0 368 506 | 5/1990 | European Pat. Off. | C12N 15/54 |
| WO89/12386 | 12/1989 | WIPO | A01H 1/04 |

OTHER PUBLICATIONS

Dey, P.M., *Biochemistry of Storage Carbohydrates in Green Plants*, P.M. Dey et al (Eds.), Academica Press, London, pp. 53–129 (1985).
Gitzelmann, R. et al, *Pediatrics*, 36(2), 231–236 (1965).
Ruttloff, H. et al, *Die Nahrung*, 11, 39–46 (1967).
Murphy, E.L. et al, *J. Agr. Food Chem.*, 20(4), 813–817 (1972).
Cristofaro, E. et al, *Sugars in Nutrition*, H.L. Sipple et al (Eds.), Academic Press, NY, Chap. 20 (1974).
Ocharov, K.E. et al, *Fiziol. Rast.*, 21(5), 969–974 (1974).
Caffrey, M. et al, *Plant Physiol.*, 86, 754–758 (1988).
Schleppi, P. et al, *Iowa Seed Science*, 11(2), 9–12 (1989).
Parker, J., *Bot. Gaz.*, 121, 46–50 (1959).
Alden, J. et al, *Bot. Rev.*, 37, 37–142 (1971).
Kandler, et al, *Ency. of Plant Physiology*, New Series, 13A, 348–383 (1982).
Castillo, E.M. et al, *J. Agric. Food Chem.*, 38(2), 351–355 (1990).
Saravitz, D.M. et al, *Plant Physiol.*, 83, 185–189 (1987).
Smith, P.T. et al, *Plant Physiol*, 96, 693–698 (1991).
Aebersold, R.H. et al, *Proc. Natl. Acad. Sci. USA*, 84, 6970–6974 (1987).
Jaye, M. et al, *Nucleic Acids Research*, 11(8), 2325–2335 (1983).
Hinchee, M.A.W. et al, *Biotechnology*, 6, 915–922 (1988).
Schuler, M.A. et al, *Nucleic Acids Research*, 10(24), 8225–8244 (1982).
Reeck, G.R. et al, *Cell*, 50, p. 667 (1987).
Dorel, C. et al, *J. of Cell Biology*, 108, 327–337 (1989).
Beebe, D.U. et al, *Plant Physiology*, 96(1), p. 100(1991).
Sambrook, et al, *Molecular Cloning: A Laboratory Manual*, 2nd ed., pp. 12.10–12.28 (1990).
Saravitz, D.M. et al, *Biological Abstracts*, 83, Abstract. No. 101203 (1987).
Dilworth, M.F., *The Plant Cell*, 3(3), 213–218 (1991).
Smith, P.T. et al, *Plant Physiology*, 96(1), p. 9 (1991).
James, *Antiviral Chemistry and Chemotherapy* 2: 191–214 1991.
Gura, *Science* 270: 575–577 1995.
P. Sijmons et al. *Bio/Technology*, vol. 8 (Mar. 1990) pp. 217–221.
D. Grierson et al., in Lycett & Girerson (eds.) *Genetic Engineering of Crop Plants*, (London, Butterworks, 1990) pp. 115–125.
S. Tanksley et al. *Bio/Technology*, vol. 7 (Mar. 1989) pp. 257–264.
Kuo et al, *Plant Physiol* 99:72, 1992.

*Primary Examiner*—W. Gary Jones
*Assistant Examiner*—Dianne Rees

[57] ABSTRACT

There is provided isolated nucleic acid fragments that encode soybean seed and zucchini leaf galactinol synthase. Chimeric genes including those fragments and suitable regulatory genes are also provided that are capable of transforming plants to produce galactinol synthase at levels higher or lower than that found in the target plant. Transformed plants and seeds are also provided for. Methods for varying the content of D-galactose-containing oligosaccharides of sucrose in plants are also provided.

7 Claims, 3 Drawing Sheets

NUCLEOTIDE SEQUENCES OF GALACTINOL SYNTHASE FROM ZUCCHINI AND SOYBEAN

This application is a 371 application of PCT/US92 06057 filed Jul. 24, 1992.

BACKGROUND OF THE INVENTION

Raffinose saccharides are a group of D-galactose-containing oligosaccharide derivatives of sucrose that are widely distributed in plants. Raffinose saccharides are characterized by the general formula: [O-β-D-galactopyranosyl-$(1\rightarrow 6)_n$-α-glucopyranosyl-$(1\rightarrow 2)$-β-D-fructofuranoside where n=0 through n=4 are known respectively as sucrose, raffinose, stachyose, verbascose, and ajugose.

Extensive botanical surveys of the occurrence of raffinose saccharides have been reported in the scientific literature [see Dey (1985) in Biochemistry of Storage Carbohydrates in Green Plants, P. M. Dey and R. A. Dixon, Eds. Academic Press, London, pp. 53–129]. Raffinose saccharides are thought to be second only to sucrose among the nonstructural carbohydrates with respect to abundance in the plant kingdom. In fact, raffinose saccharides may be ubiquitous, at least among higher plants. Raffinose saccharides accumulate in significant quantities in the edible portion of many economically-significant crop species. Examples include soybean (*Glycine max* L. Merrill), sugar beet (*Beta vulgaris*), cotton (*Gossypium hirsutum* L.), canola (Brassica sp.) and all of the major edible leguminous crops including beans (Phaseolus sp.), chick pea (*Cicer arietinum*), cowpea (*Vigna unguiculata*), mung bean (*Vigna radiata*), peas (*Pisum sativum*), lentil (*Lens culinaris*) and lupine (Lupinus sp.).

Although abundant in many species, raffinose saccharides are an obstacle to the efficient utilization of some economically-important crop species. Raffinose saccharides are not digested directly by animals, primarily because α-galactosidase is not present in the intestinal mucosa [Gitzelmann et al. (1965) Pediatrics 36:231–236; Rutloff et al. (1967) Nahrung 11:39–46]. However, microflora in the lower gut are readily able to ferment the raffinose saccharides resulting in an acidification of the gut and production of carbon dioxide, methane and hydrogen [Murphy et al. (1972) J. Agr. Food. Chem. 20: 813–817; Cristofaro et al. (1974) in Sugars in Nutrition, H. L. Sipple and K. W. McNutt, Eds. Academic Press, New York, Chap. 20, 313–335; Reddy et al. (1980) J. Food Science 45:1161–1164]. The resulting flatulence can severely limit the use of leguminous plants in animal, particularly human, diets. It is unfortunate that the presence of raffinose saccharides restricts the use of legumes in human diets because many of these species are otherwise excellent sources of protein and soluble fiber. Varieties of edible beans free of raffinose saccharides would be more valuable for human diets and would more fully use the desirable nutritional qualities of edible leguminous plants.

Soybean meal is the principal source of protein in animal feed, especially feed for monogastric animals such as poultry and swine. Approximately 28 million metric tons of soybean meal were produced in the U.S. in 1988 [Oil Crops Situation and Outlook Report (April 1989) U.S. Dept. of Agriculture, Economic Research Service]. Soybean meal is produced by treating soybeans with hexane to remove the oil and then toasting the extracted material to remove the residual solvent. Although the soybean is an excellent source of vegetable protein, there are inefficiencies associated with its use that appear to be due to the presence of raffinose saccharides. Compared to maize, the other primary ingredient in animal diets, gross energy utilization for soybean meal is low [see Potter et al. (1984) in Proceedings World Soybean Conference III, 218–224]. For example, although soybean meal contains approximately 6% more gross energy than ground yellow corn, it has about 40 to 50% less metabolizable energy when fed to chickens. This inefficiency of gross energy utilization does not appear to be due to problems in digestion of the protein fraction of the meal, but rather due to the poor digestion of the carbohydrate portion of the meal. It has been reported that removal of raffinose saccharides from soybean meal by ethanol extraction results in a large increase in the metabolizable energy for broiler chickens [Coon et al. (1988) Proceedings Soybean Utilization Alternatives, University of Minnesota, 203–211]. Removal of the raffinose saccharides was associated with increased utilization of the cellulosic and hemicellulosic fractions of the soybean meal. Soybean varieties free of raffinose saccharides could be used to produce meals that would have added value for individuals who either produce soybean meal for animal feed or use soybean meal as a major component in the diets for their animals.

In addition to its use in animal diets, soybeans are used to produce enriched sources of vegetable protein for human use. Examples of soybeans in human foods include soy protein concentrate, textured soy protein and infant formula. Facilities and methods to produce protein isolates from soybeans are available across the U.S. One of the unsolved challenges faced by producers of soy protein isolates is selectively purifying the protein away from the raffinose saccharides. Considerable added costs result from removing the large amounts of raffinose saccharides that are present in soybeans. Again, soybean varieties free of raffinose saccharides would reduce the cost of producing soy protein products as well as improve the nutritional quality of the end product.

Other agronomically-important crops such as cotton and canola are also used as secondary sources of protein for animal diets. Meals produced from seeds of these species also contain raffinose saccharides. The effect of raffinose saccharides on the nutritional quality of cottonseed and canola meal has received little or no attention, but it is possible that raffinose saccharides are as great a barrier to the use of these meals as they appear to be with soybean. Both cotton and canola meal have less value than soybean meal for metabolizable energy to animals [Feedstuffs (1990) Reference Issue 62:24–31]. Varieties of cotton or canola free of raffinose saccharides may have added value for use in animal feed.

An additional problem associated with the presence of raffinose in plants occurs in the production of sucrose from sugar beets. The small amount of raffinose, ca. 0.05%, compared to sucrose, ca. 16%, in expressed beet juice is sufficient to decrease the efficiency of crystallization of sucrose. As a result, sugar manufacturers have resorted to the use of immobilized α-galactosidase to reduce the content of molasses during the refining of sugar beet juice [Linden (1982) Enzyme Microb. Technol. 4:130–136]. Sugar beet varieties free of raffinose would not need this additional processing and therefore would have added value to sugar beet processors.

Although nutritional and economic problems are associated with the presence of raffinose saccharides in many crops, certain benefits are also ascribed to this family of oligosaccharides. Seed viability has been correlated positively with the presence of raffinose [Ovacharov et al. (1974)

Fiziol. Rast. 21:969–974; Caffrey et al. (1988) Plant Physiol. 86:754–758; Schleppi et al. (1989) Iowa Seed Science 11:9–12]. It is thought that raffinose helps maintain the integrity of the membranes of seeds as they undergo the desiccation process during maturation. Raffinose also may play an important role in the cryoprotection of plants. The accumulation of raffinose in plants exposed to cold temperature has been indicated in a number of species [Parker (1959) Bot. Gaz. 121:46–50; Alden et al. (1971) Bot. Rev. 37:37–142, see Kandler et al. (1982) in Encyclopedia of Plant Physiology, New Series, Vol. 13A:348–383; Mitcham-Butler et al. (1987) J. Amer. Soc. Hort. Sci. 112:672–676; Castillo et al. (1990) J. Agric. Food Chem. 38:351–355]. This accumulation of raffinose may be responsible for protection of chloroplasts and has been shown to be highly correlated with the postharvest retention of needles in horticulturally-important coniferous species such as Fraser fir [*Abies fraseri* (Pursh) Poir.] and white pine (*Pinus strobus* L.). Retention of needles in these species affects their quality for use as ornamental plants, such as Christmas trees. Producing plants with increased amounts of raffinose saccharides may increase cold hardiness resulting in increased post-harvest quality, a greater ability to withstand cold temperatures or provide producers greater flexibility when harvesting trees.

In spite of the problems associated with the presence of raffinose saccharides in soybean products for human use, for certain food applications increasing the amount of fermentable carbohydrates present in the soybean offers some advantages. [Economic Implications of Modified Soybean Traits (1990) Special Report ISSN: 0361-199X Iowa State Report]. Examples include oriental foods such as tofu, tempeh, natto, and soy sauce. In these applications, soybean varieties with increased amounts of readily-fermentable sugars such as sucrose and the raffinose saccharides would have added value for the producers of these products.

The biosynthesis of raffinose saccharides has been fairly well characterized [see Dey (1985) in Biochemistry of Storage Carbohydrates in Green Plants, P. M. Dey and R. A. Dixon, Eds. Academic Press, London, pp. 53–129]. The committed reaction of raffinose saccharide biosynthesis involves the synthesis of galactinol from UDP-galactose and myo-inositol. The enzyme that catalyzes this reaction is galactinol synthase. Synthesis of raffinose and higher homologues in the raffinose saccharide family from sucrose is thought to be catalyzed by distinct galactosyltransferases (for example, raffinose synthase and stachyose synthase). Studies with many species suggest that galactinol synthase is the key enzyme controlling the flux of reduced carbon into the biosynthesis of raffinose saccharides [Handley et al. (1983) J. Amer. Soc. Hort. Sci. 108:600–605; Saravitz, et al. (1987) Plant Physiol. 83:185–189]. Altering the activity of galactinol synthase, either as a result of overexpression or through antisense inhibition, would change the amount of raffinose saccharides produced in a given tissue.

In order to alter the activity of galactinol synthase using molecular biological approaches it is essential to isolate the gene(s) or cDNA(s) encoding the enzyme. There are no published reports for the purification of homogeneous galactinol synthase which would allow one to prepare DNA probes based on amino acid sequence information. Applicants describe here the purification of galactinol synthase from zucchini (*Cucurbita pepo*) and the subsequent cloning and use of galactinol synthase-encoding nucleotide sequences from zucchini, soybean, and canola.

SUMMARY OF THE INVENTION

The invention can be more fully understood from the following detailed description, the accompanying drawings and the Sequence Descriptions which form a part of this application. The Sequence Descriptions contain the three letter codes for amino acids as defined in 37 C.F.R. 1,822 which are incorporated by reference herein. The citation herein of any patents, pending U.S. applications, and any other disclosure that was available to the public as of the filing date of the instant application are incorporated herein by reference in their entirety.

A means has been discovered to produce transgenic plants and microorganisms in which a galactinol synthase gene overexpresses or underexpresses yielding raffinose saccharides in altered (higher than normal or lower than normal) levels as compared to non-transgenic plants or microorganisms. Transgenic plants that produce higher than normal levels of raffinose saccharides possess enhanced cold tolerance and in coniferous species will result in reduced postharvest needle abscission. Transgenic plants that produce lower than normal levels of raffinose saccharides are more easily digestible and have available larger amounts of metabolizable energy. In sugar beets in particular, a decrease in raffinose saccharide content would improve sucrose crystallization and overcome the need for expensive processing of sugar beet extracts.

One aspect of the invention is an isolated nucleic acid fragment comprising a nucleotide sequence encoding plant galactinol synthase. The fragment is derived from soybean, zucchini, canola, cotton, edible legumes, sugar beet, coniferous horticulatural species, Stachys, maize or tobacco. More prefereably, the fragment is derived from soybean, zucchini, or canola.

Another aspect of the invention is an isolated nucleic acid fragment comprising a nucleotide sequuences corresponding to or substantially homologous to SEQ ID NO: 5 or SEQ ID No: 6 encoding plant galactinol synthase.

Another aspect of the invention is a chimetic gene capable of being expressed in transformed plants that comprises an isolated nucleotide sequence encoding plant galactinol synthase and suitable regulatory sequences such that upon transformation said plant overexpresses raffinose saccharides relative to non-transformed plants. A related aspect of the invention is a chimetic gene capable of being expressed in transformed plants that comprises an isolated nucleotide sequence encoding antisense RNA complementary to plant galactinol synthase and suitable regulatory sequences such that upon transformation said plant underexpresses raffinose saccharides relative to non-transformed plants. A further aspect of the invention is a chimetic gene capable of being expressed in transformed microorganisms comprising nuceic acid fragments encoding plant galactinol synthase and suitable regulatory sequences.

A further aspect of the invention is a host cell transformed with a chimetic gene capable of being expressed in transformed plants, the gene comprising a nucleotide sequence encoding plant galactinol synthase and a suitable regulatory sequence.

An additional aspect of the invention is a plant transformed with a chimeric gene capable of being expressed in transformed plants, the gene comprising a nucleotide sequence encoding plant galactinol synthase and a suitable regulatory sequence. Such transformed plant overexpresses or underexpresses raffinose saccharides relative to non-transformed plants. Such transformed plant is a higher plant including soybean, zucchini, canola, cotton, edible legumes, sugar beet, coniferous horticultural species, Stachys, maize and tobacco. More preferably, the transformed plant is soybean, zucchini or canola.

A further important aspect of the invention is seed obtained from plants transformed with a chimetic gene capable of being expressed in transformed plants, the gene comprising a nucleotide sequence encoding plant galactinol synthase and a suitable regulatory sequence. Such seeds are obtained from transformed plants including transformed soybean, zucchini, canola, cotton, edible legumes, sugar beet, coniferous horticultural species, Stachys, maize and tobacco. More preferably, the transformed plant is soybean, zucchini or Canola.

A further aspect of the invention is a microorganism transformed with a chimetic gene capable of being expressed in a microorganism, the gene comprising a nucleotide sequence encoding plant galactinol synthase and a suitable regulatory sequence. Most preferably, the transformed micoorganism is *E. coli*.

Another aspect of the invention is a method for obtaining plants and plant cells containing altered (higher or lower than that of non-transformed plants) levels of raffinose saccharides and or sucrose. This method is performed by (a) transforming a plant cell with a chimetic gene that encodes antisense RNA complementary to galactinol synthase;

(b) growing fertile plants from said transformed plant cell; and (c) screening progeny plants for the desired levels of raffinose saccharides.

A further aspect of the invention is a method for producing galactinol. This method involves (a) transforming *E. coli* with the chimetic gene of claim 5;

(b) growing said *E. coli* under conditions suitable for expression of galactinol synthase;

(c) isolating a galactinol synthase enzyme from the *E. coli* of step (b); and (d) contacting said isolated galactinol synthase enzyme with appropriate substrates in order to produce galactinol.

A further aspect of the invention is another method for producing galactinol. This method involves (a) isolating a galactinol synthase enzyme from a plant; and (b) contacting said isolated glactinol synthase enzyme with appropriate substrates in order to produce galactinol.

An aspect of this invention is a method of RFLP breeding to produce altered levels of raffinose saccharides and sucrose traits in soybeans. This method involves (a) crossing between two soybean varieties differing in the traits for raffinose saccharides and sucrose levels;

(b) making a Southern blot of restriction enzyme digested genomic DNA isolated from several progeny plants resulting from the cross of (a); and (c) hybridizing the Southern blot with the radiolabelled nucleic acid fragment comprising a nucleotide sequence encoding plant galactinol synthase.

A further aspect of this invention is a method of varying the level of D-galactose containing oligosaccharides or sucrose in plants in response to end-user requirements. This method involves (a) combining the nucleic acid fragment of SEQ ID NO:5 or 6 with suitable regulatory sequences for expression and localization in plant tissues;

(b) transforming a plant cell with the product of step (a);

(c) regenerating plants from said transformed plant cell of step (b) to obtain mature plants;

(d) screening the seeds of the plants of step (c) for the desired variation in amino acid level.

BRIEF DESCRIPTION OF THE SEQUENCE LISTINGS

SEQ ID NOs:1–4 show the nucleotide sequences for four degenerate oligonucleotides used in PCR of zucchini cDNA.

SEQ ID NO:5 shows the nucleotide sequence of zucchini leaf galactinol synthase cDNA. The nucleotide 1 is the first nucleotide following the Eco R1 restriction site used in cloning the cDNA, reading from 5' to 3' on the cDNA insert, and nucleotide 1265 is the last nucleotide of the cDNA insert, immediately before the first nucleotide of the Xho1 restriction cloning site of plasmid p812. Nucleotides 1 to 32 are the 5' untranslated sequence, nucleotides 33 to 35 are the translation initiation codon, nucleotides 1023 to 1025 are the termination codon, and nucleotides 1026 to 1265 are the 3' untranslated sequence.

SEQ ID NO:6 shows the nucleotide sequence of soybean seed galactinol synthase cDNA. The nucleotide 1 is the first nucleotide following the Pst 1 restriction site, reading from 5' to 3' on the cDNA insert, nucleotide 1406 is the last nucleotide of the cDNA insert, immediately before the first nucleotide of the Kpn 1 restriction site of plasmid pS21. Nucleotides 1 to 138 are the 5' untranslated sequence, nucleotides 139 to 141 are the translation initiation codon, nucleotides 1123 to 1125 are the termination codon, and nucleotides 1126 to 1406 are the 3' untranslated sequence.

SEQ ID NOs:7–10 show amino acid sequences of peptide fragments from zucchini leaf galactinol synthase. SEQ ID NOs:7–9 are internal peptide fragments generated via CNBr cleavage. SEQ ID NO:10 is the amino acid sequence of the N-terminus of the galactinol synthase holoenzyme.

SEQ ID NO:11 shows the 5' junction between the vector and insert sequences of p812.

SEQ ID NO:12 shows converted 5' junction between vector and insert sequences of p8125, resulting in an open reading frame.

DETAILED DESCRIPTION OF THE INVENTION

The present invention describes two nucleic acid fragments that encode soybean seed and zucchini leaf galactinol synthase. These enzymes catalyze the synthesis of galactinol. The only known function of galactinol is as the galactosyl donor in raffinose saccharide biosynthesis. Transfer of either of these nucleic acid fragments or portions thereof that encode a functional enzyme with suitable regulatory sequences into a living cell will result in the production or over-production of galactinol synthase, Transfer of the nucleic acid fragment encoding galactinol synthase in soybean into a soybean plant with suitable regulatory sequences that transcribe the antisense RNA complementary to the mRNA, or its precursor, will result in the inhibition of the expression of the endogenous galactinol synthase gene and, consequently, in reduced amounts of galactinol synthase relative to the untransformed soybean.

Following transformation of an appropriate cell host such as *E. coli* with the instant nucleic acid fragments, galactinol synthase can then be overexpressed relative to the untransformed host cell. Subsequent isolation and contact of the enzyme with the appropriate substrates results in the production of galactinol.

The instant soybean nucleic acid fragments can also be used as restriction fragment length polymorphism (RFLP) markers in soybean genetic studies and breeding programs.

In the context of this disclosure, a number of terms shall be utilized. As used herein, the term "nucleic acid" refers to a large molecule which can be single stranded or double stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. As used herein, the term "homologous to" refers to the complementarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art [as described in Hames and Higgins, Eds. (1985) Nucleic Acid Hybridisation, IRL Press, Oxford, U.K.]; or by the comparison of sequence similarity between two nucleic acids or proteins. As used herein, "substantially homologous" refers to nucleic acid molecules which require less stringent conditions of hybridization than those for homologous sequences, and coding DNA sequence which may involve base changes that do not cause a change in the encoded amino acid, or which involve base changes which may alter an amino acid, but not affect the functional properties of the protein encoded by the DNA sequence.

Thus, the nucleic acid fragments described herein include molecules which comprise possible variations of the nucleotide bases derived from deletion, rearrangement, random or controlled mutagenesis of the nucleic acid fragment, and even occasional nucleotide sequencing errors so long as the DNA sequences are substantially homologous.

"Gene" refers to a nucleic acid fragment that expresses a specific protein, including regulatory sequences preceding (5' non-coding) and following (3' non-coding) the coding region. "Galactinol synthase gene" refers to a nucleic acid fragment that expresses a protein with galactinol synthase activity. "Native" gene refers to the gene as found in nature with its own regulatory sequences. "Chimeric gene" refers to a gene that comprises heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence" (i.e., lacking an intron, such as in a cDNA) or it may include one or more introns bounded by appropriate splice Junctions. An "intron" is a sequence of RNA which is transcribed in the primary transcript but which is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that include the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that may increase the efficacy of antisense RNA to block gene expression. "Ribozyme" refers to a catalytic RNA and includes sequence-specific endoribonucleases.

As used herein, "suitable regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. In artificial DNA constructs regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. In artificial DNA constructs, promoters can also be used to transcribe antisense RNA. Promoters may also contain DNA sequences that are involved in the binding of protein factors which control the effectiveness of transcription initiation in response to physiological or developmental conditions. It may also contain enhancer elements. An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Tissue-specific" or "development-specific" promoters as referred to herein are those that direct gene expression almost exclusively in specific tissues, such as leaves or seeds, or at specific development stages in a tissue, such as in early or late embryogenesis, respectively.

The term "expression", as used herein, is intended to mean the production of a functional end-product. In the case of expression or overexpression of the galactinol synthase genes it involves transcription of the gene and translation of the mRNA into precursor or mature galactinol synthase proteins. In the case of antisense inhibition it refers to the production of antisense RNA transcripts capable of preventing the expression of the target protein. "Overexpression" refers to the production of a gene product in transgenic organisms that exceeds levels of production in normal or non-transformed organisms.

As used herein, "total α-galactoside" content refers to all α-linked carbohydrate that is soluble in the solvent system described herein and is capable of being assayed using the α-galactosidase/galactose dehydrogenase method described herein. "Total raffinose saccharides" refers to the α-galactose content present in the sum of stachyose (2 mol α-galactose/mol), raffinose (1 mol α-galactose/mol), and galactinol (1 mol α-galactose/mole) as determined by methods described herein.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Transformation" herein refers to the transfer of a foreign gene into the genome of a host organism and its genetically stable inheritance. "Restriction fragment length polymorphism" (RFLP) refers to different sized restriction fragment lengths due to altered nucletode sequences in or around variant forms of genes.

"Edible legumes" herein refers to the major edible leguminous crops including beans (Phaseolus sp.), chick pea (*Cicer arietinum*), cowpea (*Vigna unguiculata*), mung bean (*Vigna radiata*), peas (*Pisum sativum*) lentil (*Lens culinaris*) and lupine (Lupinus sp.).

"Coniferous horticultural species" herein refers to Fraser fir [*Abies fraseri* (Pursh) Poir.] and white pine (*Pinus strobus*).

Purification of Zucchini Leaf Galactinol Synthase

Galactinol synthase was purified to a 35 kD doublet when analyzed by SDS polyacrylamide gel electrophoresis (SDS-PAGE) starting from the soluble fraction of extracts made from zucchini leaves. The extract was filtered, chromatographically separated on a DE-52 cellulose column, ammonium sulfate precipitated, chromatographically separated over Phenyl-Sepharose, passed over an SPECTRA/GEL® AcA 54 gel filtration column (Spectrum) and separated via a Mono-Q column (Pharmacia). In a typical preparation, the galactinol synthase activity was purified about 800-fold. The individual 35 kD bands visualized by SDS-PAGE were separated via Mono-Q chromatography. Activity was detected from both peptides. The individual peptides were concentrated using an Amicon CENTRICON® and analyzed for amino acid composition. Results from this analysis indicated very similar if not identical composition. Approximately 700 μg of the 35 kD doublet was cut from a gradient polyacrylamide gel (10–20% acrylamide) following electrophoresis. The protein was sent for antibody production in New Zealand White rabbits by Hazelton Research Products Inc., Denver, Pa.

Cloning of the Zucchini Leaf Galactinol Synthase cDNA

Both N-terminal and internal amino acid sequence information was obtained for the zucchini leaf holoenzyme. The internal sequence information consisted of three peptides obtained from three fractions separated using a Vydac $C_4$ reversed-phase column, following Mono-Q. These fractions were named peaks A, B, and C. Two of the peptides differed by a stretch of four additional residues which was present only in the peptide in peak B. Hence, only the amino acid sequence from peaks A and C were used for oligonucleotide design.

The amino acid sequence information obtained for the individual peptides was used to design oligonucleotides for use as polymerase chain reaction (PCR) primers. However, the order of peptides relative to each other in the protein was not determined. Hence, primers for sense and antisense orientation were required for both peak A and peak C. Four degenerate oligonucleotides were designed with restriction enzyme sites at the ends to facilitate cloning of the product(s) into a suitable vector.

cDNA for the PCR was generated via the action of reverse transcriptase on poly A+ RNA previously isolated from zucchini leaves. Using oligo $(dT)_{15}$ primer, a collection of cDNAs was synthesized representing the various lengths of mRNAs in the sample. This cDNA was then used as template DNA for PCR employing combinations of the degenerate oligonucleotides. The PCR using the peak A "sense" oligonucleotide and the peak C "antisense" oligonucleotide resulted in a 302 base pair (bp) product as determined by DNA sequencing following cloning into a bacterial expression vector (p300). The fragment contained both peptide sequences from peaks A and C, plus, each preceeding Met where CNBr cleavage occurred, and the excluded nucleotides which coded for known amino acids. The Ile in peak A, however, was actually a Met in the PCR product. This DNA insert was radiolabeled and used to screen a cDNA expression library made in lambda Uni-ZAP vector (Stratagene) from poly A+ RNA isolated from young zucchini leaves. Two positively-hybridizing plaques were subjected to plaque purification. Sequences of the pBluescript (Stratagene) vector, including the cDNA inserts, from each of the purified phage stocks were excised in the presence of a helper phage and the resultant phagmids used to infect E. coli cells resulting in double-stranded plasmids, p181 and p182. The plasmid, p182, contained an 842 bp EcoR1-Xho1 insert and, when translated, coded for the stretch of amino acids found from p300, at the 5' end of the insert. The 681 bp EcoR1-Hind111 fragment of this clone was radiolabelled and used to rescreen the zucchini library. Thirty positively-hybridizing plaques were identified, ten of which were carried on for further purification and phagemid excision: p411, p711, p812, p821, p1111, p1121, p1211, p1221, p1911. The cDNA insert in plasmid p812 is flanked by an EcoR1 and a Xho1 cloning site introduced by the cDNA construction, at the 5' and 3' end, respectively. The 1265 bp nucleotide sequence encodes a 351 amino acid open reading frame that includes the N-terminal sequence found in the purified protein at the eleventh amino acid of the open reading frame. A fusion protein comprising the first 16 amino acids of β-galactosidase and beginning at the first Met (the eleventh amino acid) of the zucchini leaf galactinol synthase in an appropriate plasmid is expressed in E. coli and is catalytically functional.

Cloning of Soybean Seed Galactinol Synthase cDNA

The 1265 bp insert from the zucchini galactinol synthase cDNA, p812, was radiolabelled and used to screen a cDNA expression library made in lambda Uni-ZAP vector (Stratagene) from poly $A^+$ RNA isolated from developing soybean seeds (Wye cv.). Ten positively-hybridizing plaques were purified and the phagemids excised. Restriction digest mapping indicated that one of these, pS21, contained an insert of a size expected for the gene. The cDNA insert (SEQ ID NO:6) was 1406 bp in length with a 987 bp coding sequence; the first 138 bp of the clone was 5' non-coding sequence. The insert encodes an open reading frame of 375 amino acids with the start Met as residue 47.

The Bluescript vector sequence (Stratagene), 5' to the cDNA insert, was mutagenized to place the pS21 coding sequence (SEQ ID NO:6) in frame with the β-galactosidase gene, thus allowing for the expression of a functional galactinol synthase fusion protein in *E. coli*.

A comparison between the entire amino acid sequence from the coding regions of the zucchini and soybean cDNAs revealed 74% identity and 83% identity between the internal 288 amino acids.

The fragment of the instant invention may be used, if desired, to isolate substantially homologous galactinol synthase cDNAs and genes, including those from plant species other than soybean. Isolation of homologous genes is well-known in the art.

The nucleic acid fragment of the instant invention encoding galactinol synthase, or a coding sequence derived from other cDNAs or genes for the enzyme, with suitable regulatory sequences, can be used to overexpress the enzyme in transgenic soybean as well as other transgenic species. Such a recombinant DNA construct may include either the native galactinol synthase gene or a chimetic gene. One skilled in the art can isolate the coding sequences from the fragment of the invention by using and/or creating sites for restriction endonucleases, as described in Sambrook et al. [Molecular Cloning: A Laboratory Manual 2nd Ed. (1989) Cold Spring Harbor Laboratory Press]. Of particular utility are sites for Nco I (5'-CCATGG-3') and Sph I (5'-GCATGC-3') that allow precise removal of coding sequences starting with the initiating codon ATG. For isolating the coding sequence of galactinol synthase from p812, an Nco I site can be engineered by substituting nucleotides at positions 31 and 32 with C, and nucleotide T at position 36 with G. Cutting at this engineered site along with cuts at restriction endonuclease sites near the 3' end of p812 such as the Sph 1 at 1169 allows removal of the fragment encoding the galactinol synthase protein and directional reinsertion into a properly designed vector.

Antisense RNA has been used to inhibit plant target genes in a dominant and tissue-specific manner [see van der Krol et al. (1988) Gene 72:45–50; Ecker et al. (1986) Proc. Natl. Acad. Sci. USA 83:5372–5376; van der Krol et al. (1988) Nature 336:866–869; Smith et al. (1988) Nature 334:724–726; Sheehy et al. (1988) Proc. Natl. Acad. Sci. USA 85:8805–8809; Rothstein et al. (1987) Proc. Natl. Acad. Sci. USA 84:8439–8443; Cornelissen et al. (1988) Nucl. Acids Res. 17:833–843; Cornelissen (1989) Nucl. Acid Res. 17:7203–7209; Robert et al. (1989) Plant Mol. Biol. 13:399–409].

The use of antisense inhibition of the seed enzyme would require isolation of the coding sequence for genes that are expressed in the target tissue of the target plant. Thus, it will be more useful to use the fragment of the invention to screen seed-specific cDNA libraries, rather than genomic libraries or cDNA libraries from other tissues, from the appropriate plant for such sequences. Moreover, since there may be more than one gene encoding seed galactinol synthase, it may be useful to isolate the coding sequences from the other genes from the appropriate crop. The genes that are most highly expressed are the best targets for antisense inhibition. The level of transcription of different genes can be studied by known techniques, such as run-off transcription.

For expressing antisense RNA in soybean seed from the fragment of the invention, the entire fragment of the invention may be used. There is evidence that the 3' non-coding sequences can play an important role in antisense inhibition [Ch'ng et al. (1989) Proc. Natl. Acad. Sci. USA 86:10006–10010]. There have also been examples of using the entire cDNA sequence for antisense inhibition [Sheehy et al. (1988) Proc. Nat'l. Acad. Sci. USA 85:8805–8809].

A preferred class of heterologous hosts for the expression of the coding sequence of galactinol synthase or the antisense RNA are eukaryotic hosts, particularly the cells of higher plants including soybean (*Glycine max*), zucchini, rapeseed (canola), cotton, edible legumes, sugar beet, coniferous horticultural species, Stachys maize and tobacco. Particularly preferred among the higher plants are soybean (*Glycine max*), rapeseed (*Brassica napus*) and other edible legumes. Expression in plants will use regulatory sequences functional in such plants.

The expression of foreign genes in plants is well-established [De Blaere et al. (1987) Meth. Enzymol. 153:277–291]. The origin of promoter chosen to drive the expression of the coding sequence or the antisense RNA is not critical as long as it has sufficient transcriptional activity to accomplish the invention by increasing or decreasing, respectively, the level of translatable mRNA for galactinol synthase in the desired host tissue. Preferred promoters include strong constitutive plant promoters, such as those directing the 19S and 35S transcripts in cauliflower mosaic virus [Odell et al. (1985) Nature 313:810–812; Hull and Howell (1987) Virology 86:482–493], and tissue or developmentally-specific promoters such as those for the small subunit of ribulose 1,5-bisphosphate carboxylase [Morelli et al. (1985) Nature 315:200; Broglie et al. (1984) Science 224:838; Hererra-Estrella et al. (1984) Nature 310:115; Coruzzi et al. (1984) EMBO J. 3:1671; Faciotti et al. (1985) Bio/Technology 3:241], maize zein protein [Matzke et al. (1984) EMBO J. 3:1525], and chlorophyll a/b binding protein [Lampa et al. (1986) Nature 316:750–752].

Specific timing of expression may be desirable. Chemically-inducible promoters [Hershey et al. (1990) WO 90/11361] allow the expression of a particular transgene at a specific stage of development.

Depending upon the application, it may be desirable to select promoters that are not constitutive but specific for expression in one or more tissues of the plant. Such examples include the light-inducible promoters of the small subunit of ribulose 1,5-bisphosphate carboxylase, if the expression is desired in photosynthetic tissues, or seed-specific promoters.

Particularly preferred promoters are those that allow seed-specific expression. This may be especially useful, since the seed is the portion of the plant in which the utility of the invention would be demonstrated, i.e., as low raffinose saccharide-containing animal feed, and also since seed-specific expression will avoid any potential deleterious effect in non-seed tissues. Examples of seed-specific promoters include but are not limited to the promoters of seed storage proteins, which can represent up to 90% of total seed protein in many plants. The seed storage proteins are strictly regulated, being expressed almost exclusively in seeds in a highly tissue-specific and stage-specific manner [Higgins et al. (1984) Ann. Rev. Plant Physiol. 35:191–221; Goldberg et al. (1989) Cell 56:149–160]. Moreover, different seed storage proteins may be expressed at different stages of seed development.

Expression of seed-specific genes has been studied in great detail [see reviews by Goldberg et al. (1989) Cell 56:149–160 and Higgins et al. (1984) Ann. Rev. Plant Physiol. 35:191–221]. There are currently numerous examples for seed-specific expression of seed storage protein genes in transgenic dicotyledonous plants. These include genes from dicotyledonous plants for bean β-phaseolin [Sengupta-Gopalan et al. (1985) Proc. Natl. Acad. Sci. USA 82:3320–3324; Hoffman et al. (1988) Plant Mol. Biol. 11:717–729], bean lectin [Voelker et al. (1987) EMBO J. 6: 3571–3577], soybean lectin [Okamuro et al. (1986) Proc. Natl. Acad. Sci. USA 83: 8240–8244], soybean Kunitz trypsin inhibitor [Perez-Grau et al. (1989) Plant Cell 1:1095–1109], soybean β-conglycinin [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123], pea vicilin [Higgins et al. (1988) Plant Mol. Biol. 11:683–695], pea convicilin [Newbigin et al. (1990) Planta 180:461], pea legumin [Shirsat et al (1989) Mol. Gen. Genetics 215:326]; rapeseed napin [Radke et al. (1988) Theor. Appl. Genet. 75:685–694] as well as genes from monocotyledonous plants such as for maize 15-kD zein [Hoffman et al. (1987) EMBO J. 6:3213–3221], and barley β-hordein [Marris et al. (1988) Plant Mol. Biol. 10:359–366] and wheat glutenin [Colot et al. (1987) EMBO J. 6:3559–3564]. Moreover, promoters of seed-specific genes operably linked to heterologous coding sequences in chimetic gene constructs also maintain their temporal and spatial expression pattern in transgenic plants. Such examples include *Arabidopsis thaliana* 2S seed storage protein gene promoter to express enkephalin peptides in Arabidopsis and *B. napus* seeds [Vandekerckhove et al. (1989) Bio/Technology 7:929–932], bean lectin and bean β-phaseolin promoters to express luciferase [Riggs et al. (1989) Plant Sci. 63:47–57], and wheat glutenin promoters to express chloramphenicol acetyl transferase [Colot et al. (1987) EMBO J. 6:3559–3564].

Of particular use in the expression of the nucleic acid fragment of the invention will be the heterologous promoters from several extensively-characterized soybean seed storage protein genes such as those for the Kunitz trypsin inhibitor [Jofuku et al. (1989) Plant Cell 1:1079–1093; Perez-Grau et al. (1989) Plant Cell 1:1095–1109], glycinin [Nielson et al. (1989) Plant Cell 1:313–328], β-conglycinin [Harada et al. (1989) Plant Cell 1:415–425]. Promoters of genes for α- and β-subunits of soybean β-conglycinin storage protein will be particularly useful in expressing the mRNA or the antisense RNA to galactinol synthase in the cotyledons at mid- to late-stages of seed development [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Der. Genet. 10:112–122; Naito et al. (1988) Plant Mol. Biol. 11:109–123] in transgenic plants, since: a) there is very little position effect on their expression in transgenic seeds, and b) the two promoters show different temporal regulation: the promoter for the α-subunit gene is expressed a few days before that for the β-subunit gene.

Proper level of expression of galactinol synthase mRNA or antisense RNA may require the use of different chimeric genes utilizing different promoters. Such chimetic genes can be transfered into host plants either together in a single expression vector or sequentially using more than one vector.

It is envisioned that the introduction of enhancers or enhancer-like elements into either the native galactinol synthase promoter or into other promoter constructs will also provide increased levels of primary transcription for antisense RNA or in RNA for galactinol synthase to accomplish the inventions. This would include vital enhancers such as that found in the 35S promoter [Odell et al. (1988) Plant Mol. Biol. 10:263–272], enhancers from the opine genes [Fromm et al. (1989) Plant Cell 1:977–984], or enhancers from any other source that result in increased transcription when placed into a promoter operably linked to the nucleic acid fragment of the invention.

Of particular importance is the DNA sequence element isolated from the gene for the α-subunit of β-conglycinin that can confer 40-fold seed-specific enhancement to a constitutive promoter [Chen et al. (1988) EMBO J. 7:297–302; Chen et al. (1989) Der. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a polyadenylation signal and other regulatory sequences that may be required for the proper expression of the galactinol synthase coding region can be used to accomplish the invention. This would include the 3' end from vital genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/galactinol synthase coding region combination to which it is operably linked. There are numerous examples in the art that teach the usefulness of different 3' non-coding regions.

Various methods of transforming cells of higher plants according to the present invention are available to those skilled in the art (see EPO publications 0 295 959 A2 and 0 318 341 A1). Such methods include those based on transformation vectors based on the Ti and Ri plasmids of Agrobacterium spp. It is particularly preferred to use the binary type of these vectors. Ti-derived vectors transform a wide variety of higher plants, including monocotyledonous and dicotyledonous plants, such as soybean, cotton and rape [Pacciotti et al.(1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183]. Other transformation methods are available to those skilled in the art, such as direct uptake of foreign DNA constructs [see EPO publication 0 295 959 A2], techniques of electroporation [see Fromm et al. (1986) Nature (London) 319:791] or high-velocity ballistic bombardment with metal particles coated with the nucleic acid constructs [see Kline et al. (1987) Nature (London) 327:70, and US 4]. Once transformed, the cells can be regenerated by those skilled in the art.

Of particular relevance are the recently described methods to transform foreign genes into commercially important crops such as rapeseed [see De Block et al. (1989) Plant Physiol. 91:694–701], sunflower [Everett et al. (1987) Bio/Technology 5:1201], and soybean [McCabe et al. (1988) Bio/Technology 6:923; Hinchee et al. (1988) Bio/Technology 6:915; Chee et al. (1989) Plant Physiol. 91:1212–1218; Christou et al. (1989) Proc. Natl. Acad. Sci USA 86:7500–7504; EPO Publication 0 301 749 A2].

The use of restriction fragment length polymorphism (RFLP) markers in plant breeding has been well-documented in the art [see Tanksley et al. (1989) Bio/Technology 7:257–264]. By using the nucleic acid fragment of the invention as a probe for Southern blotting, it could be shown that at least two galactinol synthase loci exist in the soybean genome. One of these has has been mapped on a soybean RFLP map [Tingey et al. (1990) J. Cell Biochem., Supplement 14E p. 291, abstract R153]. It can thus be used as a RFLP marker for traits linked to this mapped locus. This is valuable for future mapping and tracking of genes which result in agronomically important phenotypes.

EXAMPLES

The present invention is further defined in the following EXAMPLES, in which all parts and percentages are by weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions. All such modifications are intended to fall within the scope of the appended claims.

Example 1

Cloning of Zucchini Leaf Galactinol Synthase cDNA

Galactinol Synthase Assay

Galactinol synthase activity was determined using an isotopic assay previously described by Pharr et al. [(1981) Plant Sci. Lett. 23:25–33; Handley et al. (1982) Z. Pflanzenphysiol. Bd 108 S. 447–455] with modifications of the reaction mixture and temperature. The complete reaction mixture contained enzyme extract (15 µL), UDP-{U-$^{14}$C}galactose (0.1 µmol, 1.0 µCi/µmol) (Amersham), myo-inositol (2.0 µmol), MnCl$_2$ (0.1 µmol), dithiothreitol (DTT), 1.0 µmol) and 3-(N-morpholino)-propanesulfonic acid (MOPS)/NaOH buffer at pH 7.0 (5.0 µmol), in a total volume of 100 µL. The incubation temperature was 25° C., and the reactions were terminated after 10 min. ScintiVerse Bio HP (Fisher) scintillation fluid (10 mL) was added to 300 µL of the assay mix plus enzyme extract and radioactivity in the unbound carbon was determined by scintillation counting.

An additional spectrophotometric assay was developed for use in assaying enzyme fractions purified through the Phenyl-Sepharose (Pharmacia) column. The assay mixture consisted of 1 mM UDP-galactose, 20 mM myo-inositol, 1 mM MnCl$_2$, 25 mM MOPS/NaOH (pH 7.0) 20 units/mL nucleoside diphosphokinase, 40 units/mL pyruvate kinase, 62.5 units/mL lactate dehydrogenase, 0.15 mM NADH, 1 mM ATP and 0.4 mM PEP. All components were purchased from Sigma. Comparative assays for each sample were routinely done using the above assay mixture excluding the myo-inositol. A 1:10 mixture of enzyme extract to assay mixture was made and monitored at 340 nm for 5 min at 25° C.

Purification of Zucchini Leaf Galactinol Synthase

Leaves from 3–4 week old hybrid zucchini plants (500 g, Burpee-"The Gardener's Favorite") were harvested and stored at −80° C. until use. Frozen leaves were added to 2000 mL of a buffer consisting of 50 mM MOPS/NaOH (pH 7.0), 10 mM DTT, 2 mM MnCl$_2$, and 1 mM phenylmethylsulfonyl fluoride (PMSF) and ground with a Brinkmann Polytron until thawed and homogenized. The homogenate was filtered through cheesecloth and precipitated at 4° C. by stirring in ⅓ the volume of 50% PEG 8000 for 20 min and centrifuged at 13,000×g for 20 min. The supernatant was applied to a 500 mL DE-52 radial flow column (Sepragen).

Fractions were eluted with 6 L of a NaCl gradient stepped from 0–0.5M, at a flow rate of 250 mL/min. Fractions with high enzymatic activity were adjusted to 20% saturation with ammonium sulfate, applied to a 100 mL Phenyl-SEPHAROSE™ radial flow column and eluted with 300 mL of an ammonium sulfate gradient stepping down from 20–0%, followed by 650 mL of the MOPS buffer described above. Fractions with high activity were concentrated as previously described and applied to a 2.5×90 cm SPECTRA/GEL® AcA 54 gel filtration column (Spectrum) and eluted with 50 mM MOPS/NaOH (pH 7.0), 0.2M NaCl, 2 mM DTT at a flow rate of 1 mL/min. Using a Centricon CENTRIPEPS® (10,000) the high-activity fractions were concentrated and dialyzed overnight against 50 mM MOPS (pH 7.0) and 2 mM DTT at 4° C. The sample was then applied to a 5/5 Mono-Q column (Pharmacia) and eluted with a 60 mL NaCl gradient stepping from 0–0.375M in 50 mM MOPS/NaOH (pH 7.0) and 2 mM DTT. The high-activity fractions were concentrated to 50 µL using a Amicon Centricon. The samples were stored at −80° C. in 25% glycerol.

N-Terminal and Internal Amino Acid Sequence from the Zucchini Leaf Galactinol Synthase The peak fractions of a zucchini leaf prep from the Mono-Q column were pooled and concentrated to 1 mL. The entire sample was loaded onto a Vydac C$_4$ (reversed phase) column. The column was eluted with a gradient from 100% A buffer (0.1% trifluoroacetic acid (TFA) in water) to 40% B buffer (0.1% TFA in acetonitrile) in 5 min. From 5 to 30 min the buffer was increased to 50%. Fractions #21–25 were collected and concentrated to 200 µL (from 1 mL) using a nitrogen stream. Two hundred µL of 9M guanidine-HCl, 1 mM EDTA, 0.375M Tris (pH 8.5) and 4 µL of 1.4M β-mercaptoethanol in water were added to the concentrate. The solution was incubated at 37° C. for 30 min. Four µL of 4-vinylpyridine were added and the solution was incubated at room temperature for 3 h. The solution was then loaded onto a Vydac C$_4$ column and eluted with the above gradient. The alkylated galactinol synthase peak, which eluted between 16–20 min, was collected and concentrated to 200 µL as described above. Seven hundred µL of 88% formic acid and 200 µL of 20 mg/mL cyanogen bromide (CNBr) in 70% formic acid was added to the sample. The mixture was incubated at room temperature overnight, under nitrogen. The sample was then applied to the Vydac C$_4$ column and eluted with a gradient from 100% buffer A for 5 min, and then, by increasing buffer B from 0% to 90% for 85 min. One mL fractions were collected. Five major peak fractions were pooled as follows: Peak A=#31–32, Peak B=#41, Peak C=#44–45, Peak D=#51, Peak S=#52. Each peak was concentrated to 100 µL, as described above. Protein sequence analysis was performed using an Applied Biosystems 470A Gas Phase Sequencer. Phenylthiohydantoin (PTH) amino acids were analyzed on an Applied Biosystems 120 PTH Amino Acid Analyzer. Peaks A, B, and C contained sufficient material to obtain sequence information. The peptide from peak A gave the following sequence from its N-terminal: Pro-Asn-Gly-Tyr-Phe-Tyr-Ala-Val-Ile-Asp (SEQ ID NO:7). Peak B gave the following sequence: Tyr-Phe-Asn-Asp-Ile-Tyr-Lys-Pro-Ile-Pro-Xaa-Ile-Tyr-Asn (SEQ ID NO:8). Peak C gave the following sequence: Tyr-Phe-Asn-Asp-Ile-Tyr-Lys-Pro-Ile-Pro (SEQ ID NO:9). The identity of the Xaa residue in peak B was not determined.

To obtain the N-terminal sequence of the holoenzyme, Mono-Q-purified enzyme was loaded onto a 10–20% acrylamide gradient gel and subjected to electrophoresis. The developed gel was electrophoretically blotted onto Immobilon membrane (Millipore), stained with coomassie blue and destained. The 35 kD band was cut from the Immobilon and the N-terminus was determined by gas phase sequencing as described above. The entire sequence obtained for the fragment is as follows: Pro-Ala-Ala-Thr-Glu-Thr-Ala-Ile-Glu-Xaa-Thr-Asp-Ala-Pro-Lys-Arg-Ala-Phe-Val (SEQ ID NO:10).

Cloning of the Zucchini Leaf Galactinol Synthase cDNA

Four degenerate oligonucleotides were designed from the amino acid sequences obtained from peak A and peak C for use as polymerase chain reaction (PCR) primers. The degenerate oligocleotides were designed with flanking restriction enzyme recognition sequences and sense and antisense orientations were synthesized for each peptide sequence:
Peak A sense
Peak A antisense
Peak C sense
Peak C antisense
The oligonucleotides were synthesized on an Applied Biosystems 394 DNA/RNA Synthesizer:

pestle. To the tissue, 5 mL of chloroform, 5 mL of vanadyl ribonucleoside complex (Bethesda Research Laboratories) and 100 mL of guanidine thiocyanate (GTC) reagent [3M GTC, 10 mM Tris/HCl (pH 8.0), 20 mM EDTA] was added. The mixture was centrifuged at 15,000 RPM in a Sorval SS34 rotor for 10 min at room temperature. The supernatant was then layered over 5 mL pads of 5.7M CsCl (made up in 100 mM EDTA, pH 7.6) in 9/16"×3½" polyallomer ultracentrifuge tubes. The samples were centrifuged at 28,000 RPM in a Beckman SW28 rotor for 18 h at 20° C. The supernatant was removed by aspiration. The RNA pellets at the bottom of the tubes were dissolved in a total of 2 mL of TES buffer [10 mM Tris/HCl (pH 7.4), 5 mM EDTA, 1% SDS]. The RNA was extracted with an equal volume of chloroform:n-butanol (4:1) and precipitated overnight with ethanol, and, 1/10 volume of 3M sodium acetate. The RNA was washed with 70% ethanol, dried down and redissolved in 0.5 mL of water. Poly $A^+$ RNA was isolated using poly (U) SEPHADEX® (Bethesda Research Laboratories) according to instructions supplied by the vendor. Ten µg of poly $A^+$ RNA was sent to Stratagene for construction of a lambda Uni-ZAP cDNA library. Titering of the library upon its arrival indicated that it contained $1.7 \times 10^7$ plaque-forming units (pfu)/ µL of amplified library stock.

| 5'-GCGGCCGC | ATG | CCA | AAY | GGR | TAY | TTY | TAY | GC-3' | | | | (SEQ ID NO: 1) |
|---|---|---|---|---|---|---|---|---|---|---|---|---|
| | | Pro | Asn | Gly | Tyr | Phe | Tyr | Ala | Val | Ile | Asp | (SEQ ID NO: 7) |
| | | | 3'-ATR | AAR | ATR | CGR | CAM | TAR | CT-5' | | | (SEQ ID NO: 2) |
| 5'-GCGGCCGC | ATG | TAY | TTY | AAY | GAY | ATH | TAY | AA-3' | | | | (SEQ ID NO: 3) |
| | | Tyr | Phe | Asn | Asp | Ile | Tyr | Lys | Pro | Ile | Pro | (SEQ ID NO: 9) |
| | | | 3'-TTR | CTR | TAR | ATR | TTY | GGW | TAR | GG-5' | | (SEQ ID NO: 4) |

A sense  M = A,C
A' antisense  W = A,T
C sense  Y = C,T
C' antisense  R = A,G
H = A,C,T Since it was not known which peptide (A or C) was closer to the N terminus of galactinol synthase, two reactions were run, using either A and. C' or C and A'. The cDNA for the PCR was generated using reverse transcriptase (Stratagene) on 5 µg of poly A+ RNA previously isolated from zucchini leaves. Using oligo (dT)$_{15}$ primer, a collection of cDNAs was synthesized according to the first strand synthesis procedure described by Promega Biotec. PCR was performed using a Perkin-Elmer Cetus kit according to the instructions of the vendor on a thermocycler manufactured by the same company. When run on a 1% agarose gel and stained with ethidium bromide, the product of the reaction employing oligomers A and C' showed a strong DNA band of approximately 300 bp. The band was cut from the gel, purified with Gene Clean (Bio 101 Corp.) according to the vendor's instructions and cloned into the pBluescript SK$^+$ vector (Stratagene). DNA sequencing was done using the appropriate complementary primers and a sequenase kit from United States Biochemicals Company according to the vendor's instructions. The 302 bp PCR product, when translated, coded for peptide sequences from peaks A and C in their entirety, including the Met residues which preceeded each peptide. A radioactive probe was made by random priming using $^{32}$P-dCTP and a random priming kit purchased from Boehringer Mannheim in order to screen a zucchini Uni-ZAP cDNA library. The library was made as follows: Leaves from the first three nodes of 3–4 week old hybrid zucchini plants (Burpee—"The Gardener's Favorite") were harvested and stored at −80° C. Frozen leaf tissue (20 g) was ground to a fine powder with a mortar and About 2000 pfu were plated per 80 mm plate on a total of 20 NZY-agar plates [Sambrook et al. (1989) Molecular Cloning: A Laboratory Manual, 2nd Ed. Cold Spring Harbor Laboratory Press] giving 40,000 total plaques. Plating was done using E. coli XL1-Blue (Stratagene) grown in NZY+ 0.2% maltose as the host and NZY-7.2% agarose as the plating medium. The plaques were absorbed onto nitrocellulose filters (Schleicher and Schuell, 0.45 mM pore size), in duplicate, denatured in 1.5M NaCl, 0.5M Tris/HCl (pH 7.5), and rinsed in 2×SSC. The filters-were blotted on Whatman 3MM paper and heated in a vacuum oven at 80° C. for 2 h to allow firm anchorage of phage DNA in the membranes. The nitrocellulose filters were screened using the radioactive probe made from the 302 bp PCR fragment. After prehybridizing at 50° C. in 1% bovine serum albumin (BSA), 0.5M NaPi pH 7.2 (NaH$_2$PO$_4$ and Na$_2$HPO$_4$), 10 mM EDTA, and 7% sodium dodecyl sulfate (SDS) for 4 h, the filters were transferred to fresh hybridization mix containing the denatured radiolabelled probe and stored overnight at 50° C. The filters were rinsed the next day under stringent conditions: 2×SSC [Sambrook et al. (1989) Molecular Cloning: A Laboratory Manual, 2nd Ed. Cold Spring Harbor Laboratory Press] at room temp for 15 min, 2×SSC-1% SDS at 50° C. for 15 min, and 1×SSC-1% SDS at 50° C. for 15 min. The filters were air-dried and placed against Kodak XAR-5 film at −70° C. From these autoradiograms, twenty hybridizing plaques were identified. These plaques were selected from the original petri plate and plated out at a dilution to yield about 100 plaques per 80 mm plate. These plaques were absorbed to nitrocellulose filters and reprobed using the same procedure. After autoradiography, only two of the original ten showed plaques. Pure clones were isolated and phagemid DNA was excised in the presence of helper phage, (p181, p182). DNA from the plasmids was isolated by the alkaline lysis miniprep procedure described in Sambrook et. al. (1989) [Molecular Cloning: A Laboratory Manual, 2nd Ed. Cold Spring Harbor Laboratory Press]. Restriction endonuclease digests of the DNA indicated that the two clones were very similar. Following sequencing with the United States Biochemicals sequence kit, as previously described, it was determined that the plasmid p182 contained an 842 bp EcoR1-Xho1 insert and, when translated, coded for the stretch of amino acids found in the translation of the 302 bp probe, at the 5' end of the insert. A 681 bp EcoR1-HindIII fragment of this clone was radiolabelled as previously described and used to rescreen 40,000 pfu from the zucchini library. Thirty positively-hybridizing plaques were identified, ten of which were selected for further purification and phagemid excision. One of these ten, p812, contained an 1265 bp nucleotide sequence which is shown in SEQ ID NO:5.

Example 5

Cloning of Soybean Seed Galactinol Synthase cDNA Using the Zucchini Galactinol Synthase cDNA Clone The 1265 bp insert of zucchini cDNA, p812 (SEQ ID NO:5), was radiolabelled as previously described, for use as a probe to screen the soybean seed cDNA library. In order to construct a library, polyA$^+$ RNA was isolated from 27 day old developing soybean seeds (Wye cv.). Ten µg of this RNA was sent to Stratagene for construction of a Uni-ZAP cDNA expression library. Upon arrival, the library was titered and determined to contain $1.2 \times 10^9$ pfu units/µL of amplified stock. Two thousand pfu were plated as described above and absorbed onto nitrocellulose filters. The filters were screened using the radioactive probe. Following autoradiography of the filters, two positively-hybridizing plaques were identified. Both were further purified and excision was performed in the presense of a helper phage as described above. Double-stranded DNA was prepared using the alkaline lysis method as previously described. Restriction analysis revealed that the two clones, pS11 and pS21, were similar. Sequence analysis of the pS21 insert, using the US Biochemicals Corp. sequenase kit as described above, indicates that although the insert unexpectedly lacked the two cloning sites, Eco R1 and Xho1, associated with the Uni-ZAP vector, it did contain a 1406 bp nucleic acid sequence (SEQ ID NO:6) encoding the soybean seed galactinol synthase.

Example 2A

Construction of Plant Gene Expression Vector Containing Soybean Galactinol Synthase Gene The 1.4 kb Kpn I fragment from pS21 was ligated into a new pBSK (Stratagene Cloning Systems) vector that had been cut with Kpn I and dephosphorylated. Plasmid pS21-1 was isolated from transformed XL1 blue cells and shown to contain the galactinol synthase coding region in the same orientation as that of the vector-borne β-galactosidase, though it was in a different reading frame. pS21-1 was digested with BamH I, a unique site in the vector, and the resulting 5' overhangs were filled in using Klenow fragment in the presence of 1 mM DNTPs. After ligation and transformation of XL1 blue cells, recombinant colonies containing pS21-1-B2 were identified that contained the galactinol synthase coding region in the correct orientation and the same reading frame as β-galactosidase.

Plasmid p35S:GAS was made by removing the β-glucuronidase coding region from plasmid pMH40 (FIG. 1) and replacing it with the galactinol synthase coding region from plasmid pS21-1-B2. To this end, plasmid pS21-1-B2 was digested to completion with the restriction endonucleases Pst I and Bfr I. The 5' and 3' overhanging ends of the resulting DNA fragments were rendered blunt by treatment with the Klenow fragment of DNA polymerase I in the presence of 1 mM dNTPs. The blunt-ended DNA fragments were then separated using polyacrylamide gel electrophoresis and the 1250 bp DNA fragment encoding galactinol synthase was recovered from the gel.

The vector pMH40 was digested to completion with the restriction endonucleases Xho I and Asp 718I and the resulting 5' overhanging ends were filled in using Klenow fragment in the presence of 1 mM dNTPs. The resulting blunt-ended vector was treated with calf intestinal alkaline phosphatase and ligated overnight with an equimolar amount of the 1250 bp galactinol synthase DNA fragment isolated above. The transformation mixture was diluted ten-fold with TE pH 7.5 and an aliquot of this dilution was used to transform commercially available competent HB101 cells. Small scale plasmid preparations performed on ampicillin-resistant colonies were analyzed by agarose gel electrophoresis after digestion with Sal I. Plasmids from colonies containing a 3.26 kbp Sal I fragment were then digested with Bfr I and Xho I to determine the orientation of the galactinol synthase insert in the plasmids. Plasmids showing a 1.7 kbp band upon digestion Bfr I and Xho I contained the galactinol synthase insert in a sense orientation with respect to the 35S promoter and one was designated p35S:GAS (FIG. 2).

The entire 35S-galactinol synthase gene was excised from p35S:GAS and cloned into the binary vector pZS194b (FIG. 3). The binary vector pZS194b is but one example of a large number of binary vectors available that could be used for this purpose. It contains a left border fragment from the octopine Ti plasmid pTiA6 and a right border fragment from pTiAch5 (van den Elzen et al., Plant Molecular Biology 5:149–154, 1985). The border fragments delimit the segment of DNA which becomes incorporated into the host plant genome during the process of Agrobacterium-mediated transformation. A chimetic marker gene (35S/NPT II/OCS) which specifies kanamycin resistance in plant cells and the β-galactosidase (Lac Z) gene intercepted by the polylinker sequence of pUC18 is positioned between the left and right border fragments.

The binary vector pZS194b was digested to completion with the restriction endonuclease Sal I and treated with alkaline phosphatase. Plasmid p35S:GAS was also digested to completion with Sal I and the digestion products were separated by agarose gel electrophoresis. The 3.26 kbp 35S:GAS DNA fragment was excised from the gel, purified using glass milk and ligated overnight with an equimolar amount of Sal I-digested and phosphate-treated pZS194b. An aliquot of the ligation mixture was then used to transform commercially available competent HB101 cells using the manufacturer's protocol. Aliquots of the transformation mixture were plated on LB agar containing 100 ug/mL kanamycin and grown overnight at 37° C. Small scale plasmid preparations made from individual kanamycin-resistant colonies were digested with Sal I and analyzed by agarose gel electrophoresis. One colony containing a plasmid consisting of the 3.26 kbp 35S:GAS fragment from p35S:GAS ligated into the Sal I site of pZS194b was designated pZS194b/35S:GAS:3'NOS.

The binary plasmid pZS194b/35S:GAS:3*NOS was mobilized from E. coli HB101 to Agrobacterium strain LBA 4404 (Hoekema, et al., Nature 303: 17.9–180, 1983) through a triparental mating procedure (Ruvkin and Ausubel, Nature 289:85–88, 1981).

Example 3

Expression of Zucchini Leaf Galactinol Synthase in E. coli

Sequences which are inserted into pBluescript and which are directionally correct and in-frame with the starting methionine of the interrupted β-galactosidase gene borne on the plasmid are capable of being expressed as fusion proteins consisting of N-terminal amino acids of β-galactosidase plus those encoded by the inserted sequence. Sequencing of p812 (SEQ ID NO:5) revealed that the cDNA insert was within the EcoR1 and XhoI sites of that plasmid and was directionally correct but out of frame with respect to the β-galactosidase sequences. To improve the production of galactinol synthase, p812 (SEQ ID NO:5) was modified to place the galactinol synthase sequences in-frame with those of β-galactosidase.

One µg of p812 was digested for 1.5 h with 10 I.U. of SmaI and then for an additional 1.5 h with 10 I.U. of EcoRI at 37° C. These digests cut the DNA at two places within the multiple cloning site of the vector Bluescript SK+ (Stratagene) and provided a linear 4.1 kb fragment which was isolated after electrophoresis on a 0.8% agarose gel. The fragment was incubated with 2 I.U. of the Klenow fragment of DNA polymerase in the presence of 25 µM dATP and 25 µM dTTP for 30 min at room temperature to fill in the EcoRI half-site. Following purification with Gene Clean (Bio 101 Corp.) according to the manufacturer's instructions, the fragment, now with two blunt ends, was re-circularized by incubating with 10 Weiss units of T4 DNA ligase overnight. Competent E. coli XL-1 Blue cells (Statagene) were transformed according to instructions provided by the vendor with ~50 ng of the ligated plasmid. Transformants were selected as ampicillin-resistant colonies after overnight growth on LB-agar plates. Five colonies were chosen and mini-preparations of plasmid DNA were made by the alkaline lysis procedure described above. Following restriction with either Eco R1 or Sma 1 and Kpn 1, the plasmids were analyzed by agarose gel electrophoresis. This analysis indicated that three of the plasmids lacked the Eco R1 and Sma 1 sites of p812 as anticipated. One of these plasmids, designated p8125, was chosen for further analysis. Sequencing of the 5' junction between the vector and insert sequences of p8125 confirmed that the EcoRI and SmaI sites had been destroyed, and that the original sequence in this region of p812,

5'-GTGGATCCCC CGGGCTGCAG GAATTCGGCA CGAGTGT-TGT-3', (SEQ ID NO:11)

had been converted to

5'-GTGGATCCCC CAATTCGGCA CGAGTGTTGT-3' (SEQ ID NO:12)

in p8125 (underlined sequences are from the pBluescript vector). These manipulations created an open reading frame encoding a fusion protein consisting of an additional 46 amino acid N-terminal extension (from the β-galactosidase and 5' non-coding zucchini sequences) fused to the 351 amino acid polypeptide of the zucchini GaS protein.

Liquid cultures of transformed E. coli XL1-Blue cell lines containing plasmids p812 or p8125, as well as untransformed XL1-Blue cells, were made by inoculating 5 mL of LB media Sambrook et. al. (1989) [Molecular Cloning: A Laboratory Manual, 2nd Ed. Cold Spring Harbor Laboratory Press] with cells from plated colonies. The media for the transformed cells also contained 100 µg/mL of ampicillin whereas the media for the untransformed cells contained 12.5 µg/mL of tetracycline. After overnight growth at 37° C., 0.5 mL of the overnight cultures were each diluted into 50 mL of LB media containing the appropriate antibiotic, and incubation at 37° C. was continued. After reaching an optical density at 600 nm of 0.6, the cultures were split in half. Isopropyl thiogalactoside (IPTG) was added to one 25 mL aliquot to give a final concentration of 1 mM; the other aliquot was not treated with IPTG. Growth of the cultures was continued for 18 h at 37° C., at which time the cells were harvested by centrifugation, weighed, and frozen at −80° C. for 1 h. The cells were resuspended in buffer containing 50 mM MOPS (pH 7.0) and 2 mM DTT using 5 mL of buffer/g cells. The cells were disrupted by probe sonication at 4° C. Cell debris was removed by centrifugation, and 5–15 µL portions of the supernatants were assayed for galactinol synthase activity in the presence and absence of myoinositol using the $^{14}$C-assay described above. Myoinositol-dependent galactinol synthase activities of the various extracts are shown below:

| Extract | IPTG | Net reaction µmol/min-g cells |
|---|---|---|
| XL1-Blue | − | 0 |
|  | + | 0 |
| p812/XL1-Blue | − | 0.04 |
|  | + | 0.25 |
| p8125/XL1-Blue | − | 20 |
|  | + | 22 |

These results confirm that, although p812-containing E. coli cells produce measurable galactinol synthase activity, the in-frame placement of galactinol synthase in the p8125 clones considerably increased the production of active, recombinant enzyme. Western blot analysis of the proteins produced by each of the cell lines corroborated this finding: p8125-containing cells produced peptides detectable by antibodies raised against zucchini galactinol synthase, but no antibody-detectable peptides were produced by plasmid-free or p812-containing cell lines.

Radiolabelled and unlabelled galactinol may be produced enzymatically by the action of galactinol synthase on UDP-galactose and myoinositol as described above. The possession of a readily available source of large quantities of recombinant galactinol synthase improves this synthesis, and will result in greater availability of this compound which has been difficult to obtain heretofore.

Example 4

Use of Soybean Seed Galactinol Sequence in Plasmid as a Restriction Fragment Length Polymorphism (RFLP) Marker The cDNA insert from plasmid pS21 was removed from the Bluescript vector by digestion with the restriction enzymes Pst1 and Kpn1 using standard conditions as described in Sambrook et al. [Molecular Cloning: A Laboratory Manual, 2nd Ed. (1989) Cold Spring Harbor Laboratory Press] and labelled with $^{32}$P using a Random Priming Kit from Bethesda Research Laboratories under conditions recommended by the manufacturer. The resulting radioactive probe was used to probe a Southern blot (Sambrook et al., [Molecular Cloning: A Laboratory Manual, 2nd Ed. (1989) Cold Spring Harbor Laboratory Press] containing genomic DNA from soybean [*Glycine max* (cultivar Bonus) and *Glycine soja* (PI81762)], digested with one of several restriction enzymes. After hybridization and washes under standard conditions [Sambrook et al., [Molecular Cloning: A Laboratory Manual, 2nd Ed. (1989) Cold Spring Harbor Laboratory Press], autoradiograms were obtained, and different patterns of hybridization (polymorphisms) were identified in digests performed with restriction enzymes Msp 1 and Bam H1. The same probe was then used to map the polymorphic pS21 loci on the soybean genome, essentially as described by Helentjaris et al. [(1986) Theor. Appl. Genet. 72:761–769]. Plasmid pS21 probe was applied, as described above, to Southern blots of Msp 1 or BamH1, digested genomic DNAs isolated from 68 F2 progeny plants resulting from a *G. max* Bonus×*G. soja* PI81762 cross. The bands on the autoradiograms were interpreted as resulting from the inheritance of either paternal (Bonus) or maternal (PI81762) pattern, or both (a heterozygote). The resulting data were subjected to genetic analysis using the computer program Mapmaker [Lander et al. (1987) Genomics 1: 174–181]. In conjunction with previously obtained data for 436 anonymous RFLP markers in soybean [Tingey et al. (1990) J. Cell. Biochem., Supplement 14E p. 291, abstract R153], position one genetic locus corresponding to the pS21 probe was positioned on the soybean genetic map.

Example 5

Production of Galactinol Using Zucchini Leaf Galactinol Synthase

Zucchini leaf galactinol synthase was prepared as described in Example 1, except the purification was stopped after the Phenyl Sepharose step and the high-activity fractions were concentrated to 100 mL and frozen. At this stage, the enzyme is of sufficient purity (1.2 I.U./mg protein) to catalyze the synthesis of galactinol in vitro from myo-inositol and UDP-galactose since interfering enzymatic activities have been removed. While UDP-galactose is commercially available, it is more expensive than UDP-glucose from commercially available sources. As a result, it is preferable to use UDP-glucose as the initial nucleotide sugar substrate and then convert it into UDP-galactose by treating it with the enzyme UDPG-4'-epimerase (EC 5.1.3.2). The pH optimum of UDPG-4'-epimerase is higher than that for galactinol synthase so galactinol was produced in a two-step reaction.

A 100-mL reaction mix was prepared that contained 20 mM N-tris[hydroxymethyl]methyl-3-aminopropanesulfonic acid (TAPS)/NaOH [8.7], 80 mM UDP-glucose, 200 I.U. UDPG-4'-epimerase, 80 mM myo-inositol, 2 mM $MnCl_2$, and 20 mM DTT. The mixture was incubated 10 minutes at 30° C., and then sufficient N-[2-hydroxyethyl]piperazine-N'-[2-ethansulfonic acid] (HEPES)/NaOH and MOPS were added to reduce the pH to 7.6 at 30° C. Following the addition of the buffers, 40 I.U. of galactinol synthase was added and the mixture was incubated for 4.5 hours at 30° C. Following the incubation, the mixture was lyophilized. The lyophilized powder was dissolved in water and purified by gel filtration on a Toyopearl TSK HW40F column, 2.6×75 cm. The mobile phase used was 0.04% sodium azide in water at a flow rate of 0.5 mL/min. Fractions were collected and analyzed for galactinol and myo-inositol by High Performance Anion Exchange Chromatography (HPAEC) using Pulsed Amperometric Detection (PAD). Fractions containing no significant contamination by myo-inositol were lyophilized while the remainder was repurified on the same column. This process was repeated until the majority of the galactinol was isolated from the myo-inositol. Following purification, the sodium azide was removed by passing the solution over a mixed-bed ion-exchange column (BioRad) according to the vendor's instructions. The galactinol was freeze-dried and stored over desiccant at −20° C. Identity of the galactinol was confirmed by enzymatic hydrolysis using α-galactosidase followed by HPAEC/PAD analysis of the products.

Example 6

Transformation of *Brassica napus* Cultivar "WESTAR" with 35S-Soybean Galactinol Synthase Gene

*Brassica napus* cultivar "Westar" was transformed with the 35S-soybean galactinol synthase gene by co-cultivation of seedling pieces with disarmed *Agrobacterium tumefaciens* strain LBA4404 carrying the binary vector pZS194b/35S:GAS:3'NOS as constructed in Example 2A.

*B. napus* seeds were sterilized by stirring in 10% Chlorox, 0.1% SDS for thirty minutes, and then rinsed thoroughly with sterile distilled water. The seeds were germinated on sterile medium containing 30 mM CaCl2 and 1.5% agar, and grown for six days in the dark at 24° C.

Liquid cultures of Agrobacteria for plant transformation were grown overnight at 28° C. in Minimal A medium containing 100 mg/L kanamycin. The bacterial cells were pelleted by centrifugation and resuspended at a concentration of $10^8$ cells/ml in liquid Murashige and Skoog Minimal Organic medium containing 100 uM acetosyringone.

*B. napus* seedling hypocotyls were cut into 5 mm segments which were immediately placed into the bacterial suspension. After 30 minutes, the hypocotyl pieces were removed from the bacterial suspension and placed onto BC-12 callus medium containing 100 uM acetosyringone. The plant tissue and Agrobacteria were co-cultivated for three days at 24° C. in dim light.

The co-cultivation was terminated by transferring the hypocotyl pieces to BC-12 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments were transferred to BS-48 regeneration medium containing 200 mg/L carbenicillin and 25 mg/L kanamycin. Plant tissue was subcultured every two weeks onto fresh selective regeneration medium, under the same culture conditions described for the callus medium. Putatively transformed calli grew rapidly during this phase; as calli reached a diameter of about 2 mm, they were removed from the hypocotyl pieces and placed on the same medium lacking kanamycin.

Shoots began to appear within several weeks after transfer to BS-48 regeneration medium. As soon as the shoots formed discernable stems, they were excised from the calli, transferred to MSV-1A elongation medium, and moved to a 16:8-hour photoperiod at 24° C.

Once shoots had elongated several internodes, they were cut above the agar surface and the cut ends were dipped in Rootone. Treated shoots were planted directly into wet Metro-Mix 350 soiless potting medium. The pots were covered with plastic bags which were removed when the plants were clearly growing—after about ten days.

Plants were grown at 20° C. under a 16:8-hour photoperiod. When the primary flowering stem began to elongate, it was covered with a mesh pollen-containment bag to prevent outcrossing. Self-pollination was facilitated by shaking the plants several times each day. Seeds derived from self-pollinations were harvested about three months after planting.

Two putative transformants, 124-6 and 124-25, were verified by Polymerase Chain Reaction and/or Southern blot assays as having been transformed by the 35S-soybean galactinol synthase gene. Seeds from these plants were subsequently analyzed for soluble carbohydrate composition according to Example 7.

Minimal A Bacterial Growth Medium
  Dissolve in distilled water:
  10.5 grams potassium phosphate, dibasic
  4.5 grams potassium phosphate, monobasic
  1.0 gram ammonium sulfate
  0.5 gram sodium citrate, dihydrate
  Make up to 979 mLs with distilled water
  Autoclave
  Add 20 mLs filter-sterilized 10% sucrose
  Add 1 mL filter-sterilized 1M MgSO4

Brassica Callus Medium BC-12
  Per liter:
  Murashige and Skoog Minimal Organic Medium (MS salts, 100 mg/L i-inositol, 0.4 mg/L thiamine; GIBCO #510-3118)
  30 grams sucrose
  18 grams mannitol
  1.0 mg/L 2,4-D
  3.0 mg/L kinetin
  0.6% agarose
  pH 5.8

Brassica Regeneration Medium BS-48
  Murashige and Skoog Minimal Organic Medium
  Gamborg B5 Vitamins (SIGMA #G1019)
  10 grams glucose
  250 mg xylose
  600 mg MES
  0.4% agarose
  pH 5.7
  Filter-sterilize and add after autoclaving:
  2.0 mg/L zeatin
  0.1 mg/L IAA Brassica Shoot Elongation Medium MSV-1A
  Murashige and Skoog Minimal Organic Medium
  Gamborg B5 Vitamins
  10 grams sucrose
  0.6% agarose
  pH 5.8

Example 7

Identification of Improved Carbohydrate Composition of Canola Lines 124-6 and 124-25

Assays for Galactinol Synthase, Raffinose Saccharides, and Soluble Carbohydrates Galactinol synthase activity was measured in seed of fertile plants that had been transformed with the 35S:Soybean GaS construction. Seeds were extracted in buffer (0.25M N-[2 [Hydroxyethyl]piperizine-N'-[2-ethanesulfonic acid], (HEPES)/NaOH at pH 8.0, 10 mM DTT and 1 mM $MnCl_2$) in a 5:1 (volume/weight) ratio. For each sample, approximately 100 mg of seed tissue was used for extraction of the enzyme. Following the addition of buffer, the seeds were ground twice for 15 sec using a tissue homogenizer. The seed extract was the centrifuged for 5 min at 15,000 g at 2° C. Galactinol synthase activity was assayed as described in Example 1.

Raffinose saccharide content was determined using two distinct assays. Total α-galactoside or raffinose saccharide content were determined on an "as is" basis for the ground material. Approximately 30 seeds from a given plant were ground in a mortar and pestle. Approximately 30 mg of the resultant powder was weighed into a 13×100 mm screw cap tube and 1.6 mL of chloroform and 1.5 mL of methanol:water (4:3, v/v) was added. The tubes were then capped, placed in racks and shaken on a rotary shaker for 150 min at 1800 rpm at room temperature. After extraction, the contents of the tubes were allowed to settle for 15 min. After settling, a 15 μL aliquot of the methanol:water phase was placed in a well of a 96 well microtiter plate and dried at 45° C. for 20 min. At this point the raffinose saccharide content was determined in one of two assays. The first involved a coupled enzymatic assay that employs α-galactosidase and galactose dehydrogenase as described previously (Schiweck and Busching (1969) Zucker 22:377–384, Schiweck and Busching (1975) Zucker 28:242–243, RAFFINOSE DETECTION KIT®, Boehringer Mannheim GMBH, Catalog Number 428 167) with modifications of the assay conditions. The modifications of the assay included addition of Bovine Serum Albumin (15 mg/mL) to the assay and α-galactosidase buffers, increasing the temperature and time of the α-galactosidase incubation from room temperature to 45° C. and 30 min, and increasing the time of the galactose dehydrogenase incubation from 20 min to 60 min and using stachyose instead of raffinose for the α-galactoside standard. After incubation, the A340 of the samples were determined on a BIO-TEK™ Model EL340 Microplate reader. The amount of a-galactosides present in the samples were determined by comparison to known quantities of the stachyose standard.

An additional assay was used to eliminate the potential for artifacts that could result from the use of an enzymatically based assay (e.g., presence of a novel inhibitor of α-galactosidase or galactose dehydrogenase in the seed), as well as to obtain more complete information of the individual soluble carbohydrates present in the seed.

A High Performance Anion Exchange Chromatography/Pulsed Amperometric (HPAEC/PAD) assay was used for determining the content of individual raffinose saccharides (e.g., stachyose, raffinose, and galactinol), as well as sucrose, the other major soluble sugar present in the seed. Conditions for the grinding and extraction of the seed were identical to those used for the previous assay. A 250 mL aliquot of the aqueous phase was removed and dried under reduced pressure at 75° C. The dried material was then dissolved in 1 mL of water, mixed vigorously for 30 sec. A 100 μL aliquot was removed and diluted to 1 mL with water. The sample was mixed thoroughly again and then centrifuged for 3 min at 10,000 rpm. Following centrifugation, a 20 μL sample was analyzed on a DIONEX™ PA1 column using 150 mM NaOH at 1.3 mL/min at room temperature. The DIONEX™ PAD detector was used with $E_1$=0.05 v, $E_2$=0.60 v and $E_3$=−0.60 v and an output range of 1 nA. Galactinol, glucose, fructose, sucrose, raffinose, and stachyose were well separated by the chromatographic conditions.

The carbohydrate content of the samples was determined by comparison to authentic standards.

Results obtained from the carbohydrate analyses were subjected to analysis of variance using the software SuperANOVA (Abacus Concepts, Inc., 1984 Bonita Avenue, Berkeley, Calif. 94704). Fisher's Protected LSD was used as the post-hoc test for comparison of means.

Using these protocols, two lines with identified with higher galactinol synthase activity in the harvested seed. Myo-inositol-dependent galactinol synthase activity of the lines are shown below:

| Line | Galactinol Synthase μmol/min/g seed |
|---|---|
| 124–6 | 251 |
| 125–25 | 253 |
| Westar | 77 |

The total α-galactoside content and the soluble carbohydrate composition of these lines are shown below:

| Line | Total α-galactoside | Stachyose | Raffinose | Sucrose | Galactinol | Total Raffinose Saccharide |
|---|---|---|---|---|---|---|
| | | | μmol/gram | | | |
| 124–6 | 31.6 | 6.0 | 5.1 | 221 | 4.8 | 22.0 |
| 124–25 | 42.3 | 12.7 | 1.4 | 253 | 0.0 | 26.9 |
| Westar | 90.8 | 29.8 | 2.7 | 180 | 2.2 | 64.5 |
| P-Value | 0.0001 | 0.0001 | 0.0644 | 0.0172 | 0.51 | 0.0002 |
| $LSD_{0.05}$ | 8.1 | 3.0 | NS | 43.5 | NS | 11.8 |

The results indicate that seed from lines 124-6 and 124-25 had about three times greater activity of galactinol synthase compared to that observed in seed from Westar. Despite the increased amount of galactinol synthase activity, the total α-galactoside content of the transformed lines was significantly less than that of Westar. This was confirmed using the HPAEC/PAD method as well, and this analysis indicated that the lower total α-galactoside content was primarily attributed to a substantially reduced stachyose content in the seed of 124-6 and 124-25. Differences in raffinose and galactinol content among the lines were not significant at the 0.05 level. In addition to the reduction in total α-galactoside and stachyose content, the sucrose content was higher in 125-6 and 125-25 compared to that from Westar. Collectively, these results were unexpected in that a reduction in the raffinose saccharide content and an increase in the sucrose content was not anticipated from transforming plants with a 35S:soybean GaS construction (SEQ ID NO:6). The mechanism whereby the transformation described herein results in canola plants with seeds that have an improved carbohydrate composition remains to be determined. Nevertheless, a significant improvement in the soluble carbohydrate composition of the seed was observed.

Figure 1:
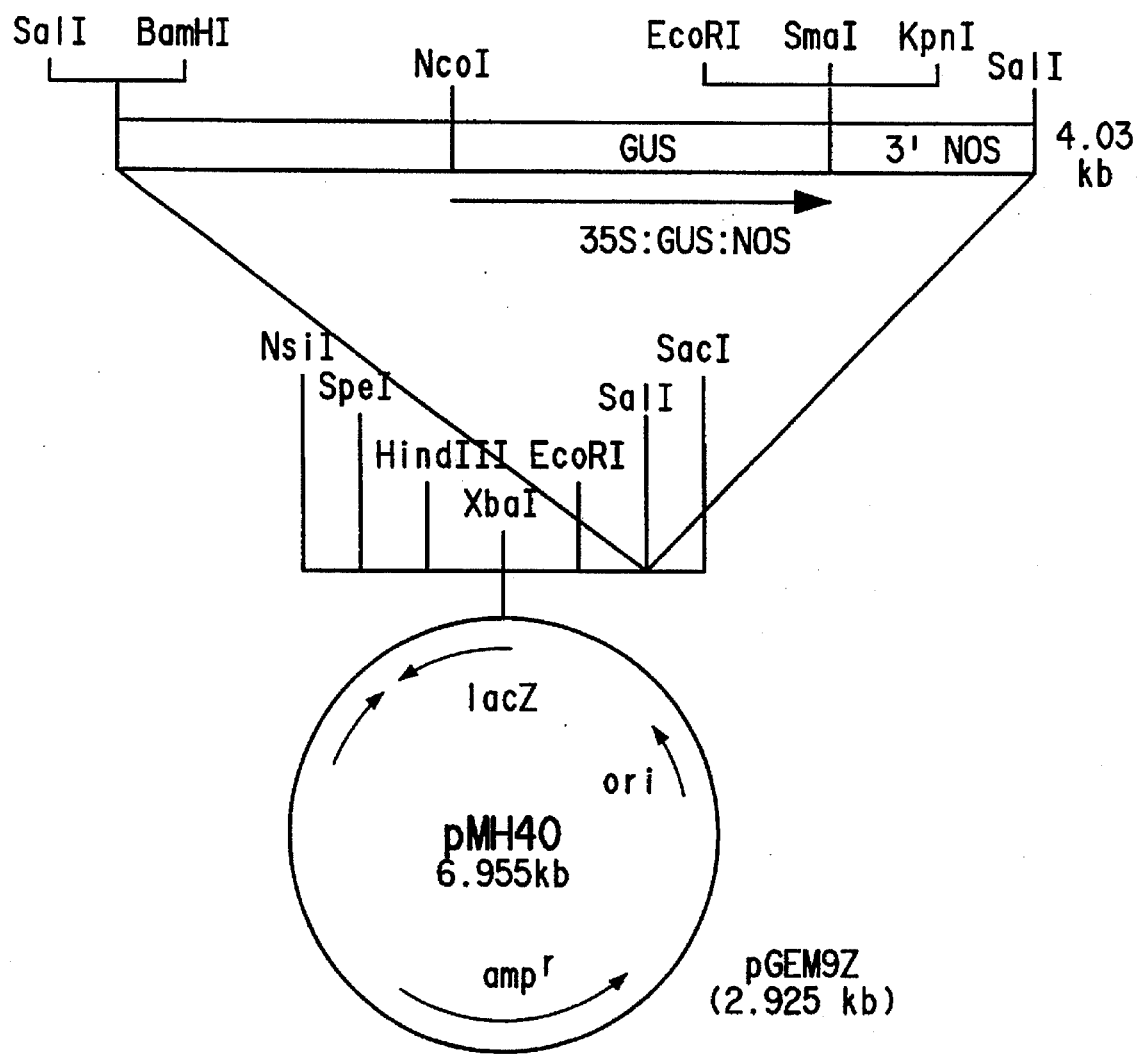
FIG. 1 shows the construction of Plasmid p35S:GAS.
Figure 2:
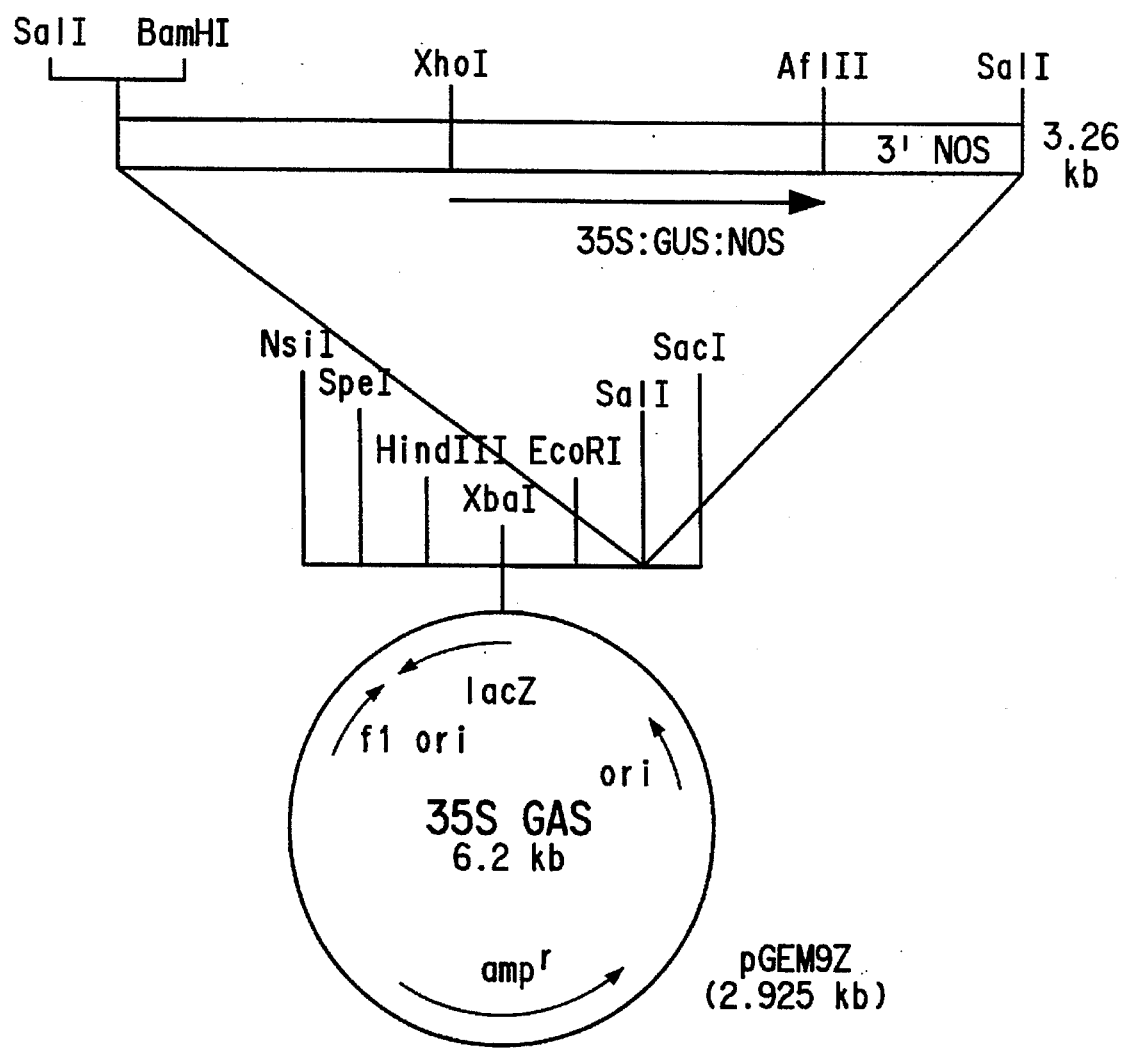
FIG. 2 shows the construction of p35S:GAS.
Figure 3:
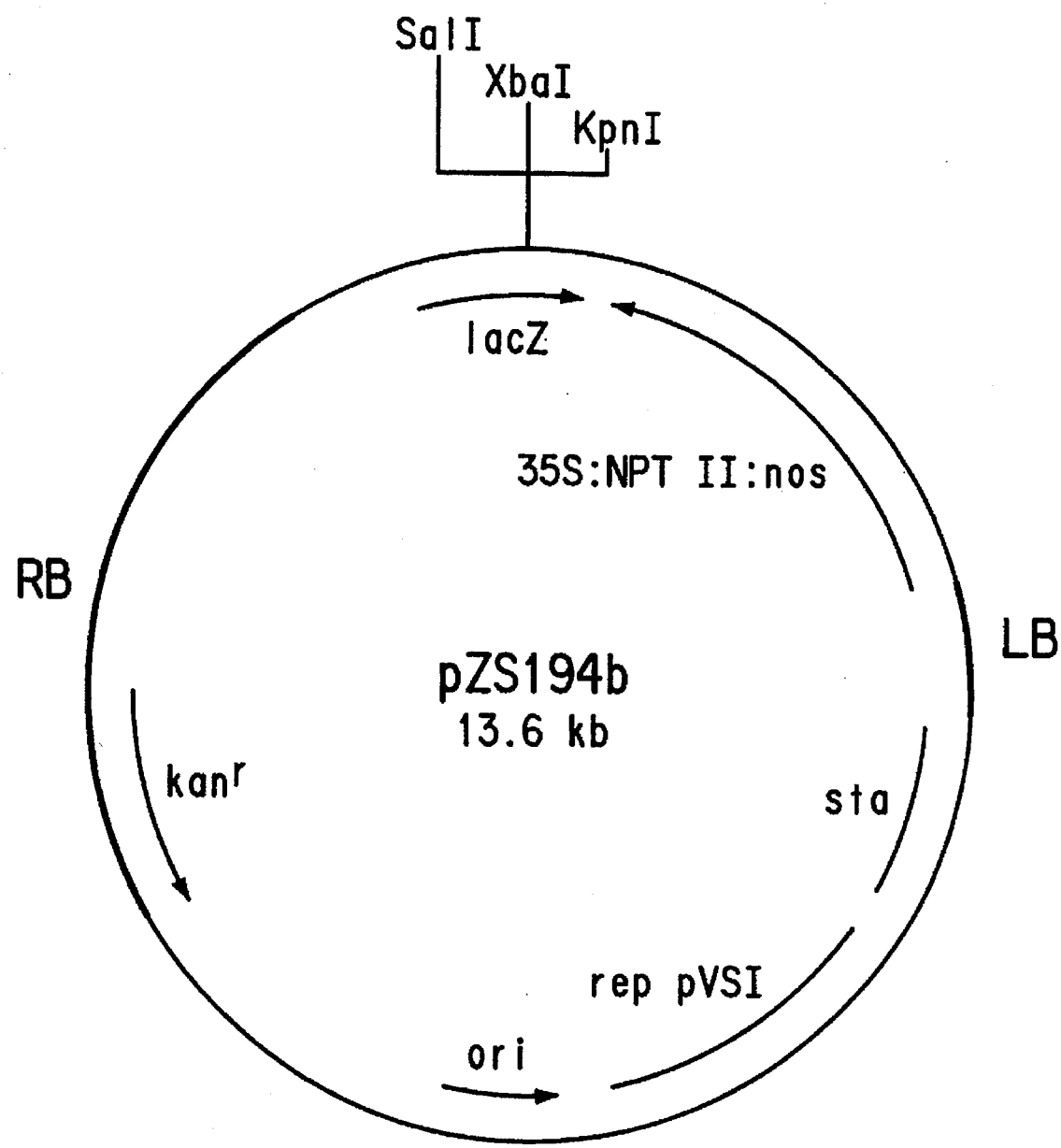
FIG. 3 shows the construction of pZS194b.

What is claimed is:

1. An isolated nucleic acid fragment consisting of a nucleotide sequence that encodes the polypeptide sequence set forth in SEQ ID NO: 5 or SEQ ID NO: 6, said polypeptide sequence encoding a plant galactinol synthase.

2. A nucleic acid fragment according to claim 1 wherein the plant is selected from the group consisting of soybean, zucchini, canola, cotton, edible legumes, sugar beet, coniferous horticultural species, Stachys, maize and tobacco.

3. A nucleic acid fragment according to claim 2 wherein the plant is selected from the group consisting of soybean, zucchini and canola.

4. A method of RFLP selection of altered levels of raffinose saccharides and sucrose traits in soybeans comprising:

(a) crossing two soybean varieties differing in the traits of raffinose saccharides and sucrose levels;

(b) making a Southern blot of restriction enzyme digested genomic DNA isolated from several progeny plants resulting from the cross of step (a);

(c) hybridizing the Southern blot with the radiolabelled nucleic acid fragment of any of claims 1–3;

(d) detecting RFLPs associated with altered levels of raffinose saccharides and sucrose traits; and (e) selecting soybean plants with altered levels of raffinose saccharides and sucrose traits.

5. An isolated nucleic acid fragment consisting of a nucleotide sequence corresponding to the nucleotide sequence set forth in SEQ ID NO:5 encoding plant galactinol synthase.

6. An isolated nucleic acid fragment consisting of a nucleotide sequence corresponding to the nucleotide sequence set forth in SEQ ID NO:6 encoding plant galactinol synthase.

7. An isolated nucleic acid fragment that is a subfragment of the nucleic acid fragment of claim 1, said subfragment consisting of at least 300 contiguous nucleotides the group of the nucleotide sequence of either SEQ ID NO: 5 or SEQ ID NO: 6.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 31 base pairs
        ( B ) TYPE: Nucleic acid
        ( C ) STRANDEDNESS: single
        ( D ) TOPOLOGY: linear ( i i ) MOLECULE TYPE: In vitro synthesized DNA ( i i i ) HYPOTHETICAL:Degenerate oligonucleotide
        encoding peptide SEQ ID NO:7

( x i ) SEQUENCE DESCRIPTION: SEQ ID NO:1:
        GCGGCCGCAT GCCAAA Y GGR TA Y TT Y TA Y G C    31

( 2 ) INFORMATION FOR SEQ ID NO:2:

( i ) SEQUENCE CHARACTERISTICS:
        ( A ) LENGTH: 20 base pairs
        ( B ) TYPE: Nucleic acid
        ( C ) STRANDEDNESS: single
        ( D ) TOPOLOGY: linear ( i i ) MOLECULE TYPE: In vitro synthesized DNA ( i i i ) HYPOTHETICAL:Degenerate oligonucleotide
        encoding peptide SEQ ID NO:7

( x i ) SEQUENCE DESCRIPTION: SEQ ID NO:2:
        T C R A T M A C R G   G R T A T A A R T A    20

( 2 ) INFORMATION FOR SEQ ID NO:3:

( i ) SEQUENCE CHARACTERISTICS:
        ( A ) LENGTH: 31 base pairs
        ( B ) TYPE: Nucleic acid
        ( C ) STRANDEDNESS: single
        ( D ) TOPOLOGY: linear ( i i ) MOLECULE TYPE: In vitro synthesized DNA ( i i i ) HYPOTHETICAL:Degenerate oligonucleotide
        encoding peptide SEQ ID NO:9

( x i ) SEQUENCE DESCRIPTION: SEQ ID NO:3:
        GCGGCCGCAT GTA Y TT Y AA Y   GA Y ATHTA Y A A    31

( 2 ) INFORMATION FOR SEQ ID NO:4:

( i ) SEQUENCE CHARACTERISTICS:
        ( A ) LENGTH: 23 base pairs
        ( B ) TYPE: Nucleic acid
        ( C ) STRANDEDNESS: single
        ( D ) TOPOLOGY: linear ( i i ) MOLECULE TYPE: In vitro synthesized DNA ( i i i ) HYPOTHETICAL:Degenerate oligonucleotide
        encoding peptide SEQ ID NO:9

( x i ) SEQUENCE DESCRIPTION: SEQ ID NO:4:
        G G R A T W G G Y T   T R T A R A T R T C   R T T    23

( 2 ) INFORMATION FOR SEQ ID NO:5:

( i ) SEQUENCE CHARACTERISTICS:
        ( A ) LENGTH: 1265 base pairs
        ( B ) TYPE: Nucleic acid
        ( C ) STRANDEDNESS: single
        ( D ) TOPOLOGY: linear (i i) MOLECULE TYPE: cDNA to mRNA (v i) ORIGINAL SOURCE:
    (A) ORGANISM: Cucurbita pepo
    (B) STRAIN: Burpee's hybrid
    (F) TISSUE TYPE: leaf (v i i) IMMEDIATE SOURCE:
    (A) LIBRARY: cDNA to mRNA
    (B) CLONE: p812

(x i) SEQUENCE DESCRIPTION: SEQ ID NO:5:

```
           GGCACGAGTG TTGTTCCACC CACATAATCA AT

ATG TcT CCG GCT GCC ACC GAA ACT GCC ATC GAg TCG ACC GAT GCC        77
Met Ser Pro Ala Ala Thr Glu Thr Ala Ile Glu Ser Thr Asp Ala
 1           5                  10                  15

CCC AAG AGG GCA TTC GTG ACG TTC TTG GCC GGT AAT GGA GAC TAT       122
Pro Lys Arg Ala Phe Val Thr Phe Leu Ala Gly Asn Gly Asp Tyr
             20                  25                  30

TGG AAA GGT GTG GTT GGA TTG GCA AAG GGT CTC AGA AAG GTC AAG       167
Trp Lys Gly Val Val Gly Leu Ala Lys Gly Leu Arg Lys Val Lys
                 35                  40                  45

ACC GTC TAC CCT CTC ATT GTA GCT GTC CTG CCT GAT GTT CCC GAA       212
Thr Val Tyr Pro Leu Ile Val Ala Val Leu Pro Asp Val Pro Glu
                     50                  55                  60

GAC CAT CGC CAG ATT CTC GAG TAT CAG GGA TGC ATC GTC CGA GAA       257
Asp His Arg Gln Ile Leu Glu Tyr Gln Gly Cys Ile Val Arg Glu
                         65                  70                  75

ATC GAG CCT GTT TAC CCC CCT GCA AAC CAG ACT CAA TTT GCG ATG       302
Ile Glu Pro Val Tyr Pro Pro Ala Asn Gln Thr Gln Phe Ala Met
                             85                  90                  95

GCA TAC TAT GTT ATC AAC TAC TCA AAG CTT AGG ATT TGG GAG TTC       347
Ala Tyr Tyr Val Ile Asn Tyr Ser Lys Leu Arg Ile Trp Glu Phe
                                105                 110                 115

GTG GAG TAT GAG AAG CTG ATA TAT TTG GAT GGG GAC ATT CAA GTG       392
Val Glu Tyr Glu Lys Leu Ile Tyr Leu Asp Gly Asp Ile Gln Val
                                    120                 125                 130

TTT GAG AAC ATC GAT CAT CTG TTC GAA ATG CCA AAT GGA TAC TTC       437
Phe Glu Asn Ile Asp His Leu Phe Glu Met Pro Asn Gly Tyr Phe
                                135                 140                 145

TAC GCC GTG ATG GAC TGC TTC TGT GAG AAG ACA TGG AGT AAC TCA       482
Tyr Ala Val Met Asp Cys Phe Cys Glu Lys Thr Trp Ser Asn Ser
                                150                 155                 160

CCG CAG TAC AAG ATT GGT TAC TGC CAG CAA TGC CCT GAC AAA GTC       527
Pro Gln Tyr Lys Ile Gly Tyr Cys Gln Gln Cys Pro Asp Lys Val
                                165                 170                 175

AAG TGG CCT GTT GAG GAA ATG GGA AAC CCA CCC CCT CTT TAC TTC       572
Lys Trp Pro Val Glu Glu Met Gly Asn Pro Pro Pro Leu Tyr Phe
                                180                 185                 190

AAC GCC GGA TTT TTT GTG TAT GAA CCC GAC CTC TTC ACC TAC AAG       617
Asn Ala Gly Phe Phe Val Tyr Glu Pro Asp Leu Phe Thr Tyr Lys
                                195                 200                 205

GAT CTT CTC GAA ACT TGC AAG GCC ACC ACT CCA ACC TTG TTT GCT       662
Asp Leu Leu Glu Thr Cys Lys Ala Thr Thr Pro Thr Leu Phe Ala
                                210                 215                 220

GAG CAG GAC TTT CTG AAC ATG TAC TTC AAC GAC ATT TAC AAA CCC       707
Glu Gln Asp Phe Leu Asn Met Tyr Phe Asn Asp Ile Tyr Lys Pro
                                225                 230                 235

ATT CCT CCC ATT TAC AAC CTC GTC ATG GCC ATG TTG TGG CGT CAT       752
Ile Pro Pro Ile Tyr Asn Leu Val Met Ala Met Leu Trp Arg His
                                240                 245                 250

CCC GAG AAC ATC GAC GTA GAC AAA GTC AAA GTT GTC CAC TAC TGT       797
```

|     |     |     |     |     |     |     |     |     |     |     |     |     |     |     |      |
| --- | --- | --- | --- | --- | --- | --- | --- | --- | --- | --- | --- | --- | --- | --- | ---: |
| Pro | Glu | Asn | Ile | Asp | Val | Asp | Lys | Val | Lys | Val | Val | His | Tyr | Cys |      |
|     |     |     |     | 255 |     |     |     | 260 |     |     |     |     |     | 265 |      |
| GCG | GCG | GGA | TCA | AAG | CCG | TGG | AGG | TAC | ACA | GGA | GAG | GAA | GAG | AAC | 842  |
| Ala | Ala | Gly | Ser | Lys | Pro | Trp | Arg | Tyr | Thr | Gly | Glu | Glu | Glu | Asn |      |
|     |     |     |     | 270 |     |     |     | 275 |     |     |     |     |     | 280 |      |
| ATG | GAC | AGA | GAA | GAC | ATA | AAA | ATG | TTG | GTG | AAG | AAA | TGG | TGG | GAG | 887  |
| Met | Asp | Arg | Glu | Asp | Ile | Lys | Met | Leu | Val | Lys | Lys | Trp | Trp | Glu |      |
|     |     |     |     | 285 |     |     |     | 290 |     |     |     |     |     | 295 |      |
| GTT | TAT | GAA | GAT | GAA | TCT | TTG | GAC | TAC | CAA | AAT | GTT | ATC | AAA | TCT | 932  |
| Val | Tyr | Glu | Asp | Glu | Ser | Leu | Asp | Tyr | Gln | Asn | Val | Ile | Lys | Ser |      |
|     |     |     |     | 300 |     |     |     | 305 |     |     |     |     |     | 310 |      |
| GAA | ACC | AAA | GAA | GCA | ACC | AAC | GTC | GCG | CCT | TTG | GTC | TCC | GTG | TTG | 977  |
| Glu | Thr | Lys | Glu | Ala | Thr | Asn | Val | Ala | Pro | Leu | Val | Ser | Val | Leu |      |
|     |     |     |     | 315 |     |     |     | 320 |     |     |     |     |     | 325 |      |
| TCG | GAG | GCT | GAA | GTT | GTC | AAC | CAT | ATC | ACA | GCT | CCT | TCT | GCT | GCT | 1022 |
| Ser | Glu | Ala | Glu | Val | Val | Asn | His | Ile | Thr | Ala | Pro | Ser | Ala | Ala |      |
|     |     |     |     | 330 |     |     |     | 335 |     |     |     |     |     | 340 |      |

TAA 1025

ATTATATATA CATATATATA TATATATATA TAGATAATAT GTATGAGTGT 1075

TTGTGGTGTG AGGCCAAATA GTATTATTAT TATTAAGCTT ATTATTATTA 1125

TGTACGGTAG CTCAGGTGGG GGTTGTTTTG TCCTTTGTGC ATGCAACTCC 1175

CAACCTTswT srykrCwwym mkTywsywwm CAAATTTTAT GAATAACCCT 1225

GCTTTTATGT GTCTTCTAA AAAAAAAAAA AAAAAAAAA 1265

( 2 ) INFORMATION FOR SEQ ID NO:6:

( i ) SEQUENCE CHARACTERISTICS:
        ( A ) LENGTH: 1406 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Glycine max
        ( B ) STRAIN: Cultivar Wye ( v i i ) IMMEDIATE SOURCE:
        ( A ) LIBRARY: cDNA to mRNA
        ( B ) CLONE: pS21

( x ) PUBLICATION INFORMATION: Unpublished ( x i ) SEQUENCE DESCRIPTION: SEQ ID NO:6:

GTTTGTTTTC AAAGTGTGTT TTGTTTCCCA AATCCTACTC TTGTGAcCAC 50

AACCCTTCCT CCTCTTTCTT TTGAAACCTC TttttttCTA TTCCCCAACC 100

AAACAAGCAA ACGCTACTCA CTCATCATCA CTGAGATC 138

|     |     |     |     |     |     |     |     |     |     |     |     |     |     |     |     |
| --- | --- | --- | --- | --- | --- | --- | --- | --- | --- | --- | --- | --- | --- | --- | ---: |
| ATG | GCT | CCT | AAT | ATC | ACC | ACT | GTC | AAA | ACC | ACC | ATC | ACC | GAC | GCT | 183 |
| Met | Ala | Pro | Asn | Ile | Thr | Thr | Val | Lys | Thr | Thr | Ile | Thr | Asp | Ala |     |
| 1   |     |     |     | 5   |     |     |     | 10  |     |     |     |     |     | 15  |     |
| CAA | GCC | AAG | GTC | GCC | ACC | GAT | CAT | GGT | CGT | GCC | TAC | GTC | ACC | TTC | 228 |
| Gln | Ala | Lys | Val | Ala | Thr | Asp | His | Gly | Arg | Ala | Tyr | Val | Thr | Phe |     |
|     |     |     |     | 20  |     |     |     | 25  |     |     |     |     |     | 30  |     |
| CTC | GCC | GGA | AAC | GGT | GAC | TAT | GTG | AAA | GGT | GTC | GTT | GGC | TTG | GCA | 273 |
| Leu | Ala | Gly | Asn | Gly | Asp | Tyr | Val | Lys | Gly | Val | Val | Gly | Leu | Ala |     |
|     |     |     |     | 35  |     |     |     | 40  |     |     |     |     |     | 45  |     |
| AAA | GGT | CTG | AGA | AAA | GTG | AAG | AGC | ATG | TAC | CCT | CTG | GTG | GTT | GCA | 318 |
| Lys | Gly | Leu | Arg | Lys | Val | Lys | Ser | Met | Tyr | Pro | Leu | Val | Val | Ala |     |
|     |     |     |     | 50  |     |     |     | 55  |     |     |     |     |     | 60  |     |

```
GTG CTA CCC GAT GTT CCC CAA GAT CAC CGC AAC ATT CTC ACC TCC      363
Val Leu Pro Asp Val Pro Gln Asp His Arg Asn Ile Leu Thr Ser
            65                  70                  75

CAA GGT TGC ATT GTT AGA GAG ATT GAG CCC GTG TAC CCC CCA GAG      408
Gln Gly Cys Ile Val Arg Glu Ile Glu Pro Val Tyr Pro Pro Glu
            80                  85                  90

AAT CAA ACC CAG TTT GCC ATG GCA TAT TAC GTC ATC AAC TAT TCC      453
Asn Gln Thr Gln Phe Ala Met Ala Tyr Tyr Val Ile Asn Tyr Ser
            95                 100                 105

AAG CTA CGT ATT TGG GAG TTT GTG GAG TAC AGC AAG ATG ATA TAC      498
Lys Leu Arg Ile Trp Glu Phe Val Glu Tyr Ser Lys Met Ile Tyr
           110                 115                 120

CTA GAC GGT GAT ATC CAA GTT TTT GAC AAC ATT GAC CAC TTG TTT      543
Leu Asp Gly Asp Ile Gln Val Phe Asp Asn Ile Asp His Leu Phe
           125                 130                 135

GAC TTG CCT GAT AAC TAC TTC TAT GCG GTG ATG GAC TGT TTC TGT      588
Asp Leu Pro Asp Asn Tyr Phe Tyr Ala Val Met Asp Cys Phe Cys
           140                 145                 150

GAG CCA ACT TGG GGC CAC ACT AAA CAA TAT CAG ATC GGT TAC TGC      633
Glu Pro Thr Trp Gly His Thr Lys Gln Tyr Gln Ile Gly Tyr Cys
           155                 160                 165

CAG CAG TGC CCC CAT AAG GTT CAG TGG CCC ACT CAC TTT GGG CCC      678
Gln Gln Cys Pro His Lys Val Gln Trp Pro Thr His Phe Gly Pro
           170                 175                 180

AAA CCT CCT CTC TAT TTC AAT GCT GGC ATG TTT GTG TAT GAG CCC      723
Lys Pro Pro Leu Tyr Phe Asn Ala Gly Met Phe Val Tyr Glu Pro
           185                 190                 195

AAT TTG GCT ACT TAC CGT GAC CTC CTT CAA ACA GTC CAA GTC ACC      768
Asn Leu Ala Thr Tyr Arg Asp Leu Leu Gln Thr Val Gln Val Thr
           200                 205                 210

CAG CCC ACT TCC TTT GCT GAA CAG GAT TTT TTG AAC ATG TAC TTC      813
Gln Pro Thr Ser Phe Ala Glu Gln Asp Phe Leu Asn Met Tyr Phe
           215                 220                 225

AAG GAC AAA TAT AGG CCA ATT CCT AAT GTC TAC AAT CTT GTG CTG      858
Lys Asp Lys Tyr Arg Pro Ile Pro Asn Val Tyr Asn Leu Val Leu
           230                 235                 240

GCC ATG CTG TGG CGT CAC CCT GAG AAC GTT GAG CTT GAC AAA GTT      903
Ala Met Leu Trp Arg His Pro Glu Asn Val Glu Leu Asp Lys Val
           245                 250                 255

AAA GTG GTT CAC TAC TGT GCT GCT GGG TCT AAG CCT TGG AGG TAC      948
Lys Val Val His Tyr Cys Ala Ala Gly Ser Lys Pro Trp Arg Tyr
           260                 265                 270

ACT GGG AAG GAG GAG AAT ATG GAG AGA GAA GAT ATC AAG ATG TTA      993
Thr Gly Lys Glu Glu Asn Met Glu Arg Glu Asp Ile Lys Met Leu
           275                 280                 285

GTG AAA AAG TGG TGG GAT ATA TAT GAG GAT GAG ACT TTG GAC TAC     1038
Val Lys Lys Trp Trp Asp Ile Tyr Glu Asp Glu Thr Leu Asp Tyr
           290                 295                 300

AAC AAT CCA CTC AAT GTG GAT AAG TTC ACT GCG GCA CTT ATG GAG     1083
Asn Asn Pro Leu Asn Val Asp Lys Phe Thr Ala Ala Leu Met Glu
           305                 310                 315

GTT GGT GAA GTC AAG TTC GTC CGT GCC CCA TCT GCT GCT TAA          1125
Val Gly Glu Val Lys Phe Val Arg Ala Pro Ser Ala Ala
           320                 325

GAGTGTCTTT GGAAATCAAG TGTGATCCAA GTACATGTAC AAAGTCATAC           1175

ATCATTACAT TAACTTTTAT GTATTCTAA AAGTCATACA TCATTACATT            1225

AAGTTTTATG TATTTCTAAA GTCTTAAGAC TTAAGAGGAC CTTTTTTATk           1275 kkkCCcGCTT TTCTTTTTTT CTTTTTCCAA TTCTGTCATT GTAAAGsrGA           1325
```

```
           GAATACCGTA  TCCTTAATTT  TATAAATGGA  TATGAATTTT  ATTTGTACTA           1375

AAGGGGGGGC  CGGTACCAAT  TCGCCTATAG  T                                1406
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: Peptide ( v ) FRAGMENT TYPE: CNBr cleavage product ( v i ) ORIGINAL SOURCE:
        ( A ) ORGANISM: Cucurbita pepo
        ( B ) STRAIN: unknown
        ( F ) TISSUE TYPE: leaf ( x ) PUBLICATION INFORMATION: unpublished ( x i ) SEQUENCE DESCRIPTION: SEQ ID NO:7:
```
              Pro  Asn  Gly  Tyr  Phe  Tyr  Ala  Val  Ile  Asp
              1                   5                        10
```

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: Peptide ( v ) FRAGMENT TYPE: CNBr cleavage product ( v i ) ORIGINAL SOURCE:
        ( A ) ORGANISM: Cucurbita pepo
        ( B ) STRAIN: unknown
        ( F ) TISSUE TYPE: leaf ( x ) PUBLICATION INFORMATION: unpublished ( x i ) SEQUENCE DESCRIPTION: SEQ ID NO:8:
```
              Tyr  Phe  Asn  Asp  Ile  Tyr  Lys  Pro  Ile  Pro
              1                   5                        10
              Xaa  Ile  Tyr  Asn
              11
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE:
        A)DESCRIPTION: Peptide ( v ) FRAGMENT TYPE: CNBr cleavage product ( v i ) ORIGINAL SOURCE:
        ( A ) ORGANISM: Cucurbita pepo
        ( B ) STRAIN: unknown
        ( F ) TISSUE TYPE: leaf ( x ) PUBLICATION INFORMATION: unpublished ( x i ) SEQUENCE DESCRIPTION: SEQ ID NO:9:
```
              Tyr  Phe  Asn  Asp  Ile  Tyr  Lys  Pro  Ile  Pro
              1                   5                        10
```

( 2 ) INFORMATION FOR SEQ ID NO:10:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE:
    (A) DESCRIPTION: Peptide (v) FRAGMENT TYPE: N-terminus (vi) ORIGINAL SOURCE:
    (A) ORGANISM: Cucurbita pepo
    (B) STRAIN: unknown
    (F) TISSUE TYPE: leaf (x) PUBLICATION INFORMATION: unpublished (xi) SEQUENCE DESCRIPTION: SEQ ID NO:10:

```
Pro Ala Ala Thr Glu Thr Ala Ile Glu Xaa
1               5                   10
Thr Asp Ala Pro Lys Arg Ala Phe Val
11              15
```

(2) INFORMATION FOR SEQ ID NO:11:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (xi) SEQUENCE DESCRIPTION: SEQ ID NO:11:
```
GTGGATCCCC CGGGCTGCAG GAATTCGGCA CGAGTGTTGT    40
```

(2) INFORMATION FOR SEQ ID NO:12:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:12:
```
GTGGATCCCC CAATTCGGCA CGAGTGTTGT    30
```